United States Patent
Holtkamp et al.

(10) Patent No.: US 9,671,357 B2
(45) Date of Patent: Jun. 6, 2017

(54) SYSTEM AND METHOD FOR MONITORING HOT GLASS CONTAINERS TO ENHANCE THEIR QUALITY AND CONTROL THE FORMING PROCESS

(75) Inventors: Mark Edwin Holtkamp, Groningen (NL); Teunis René Brummelman, EC Harkstede (NL)

(73) Assignee: Emhardt Glass S.A., Cham (CH)

( * ) Notice: Subject to any disclaimer, the term of this patent is extended or adjusted under 35 U.S.C. 154(b) by 210 days.

(21) Appl. No.: 12/963,405

(22) Filed: Dec. 8, 2010

(65) Prior Publication Data

US 2011/0141265 A1   Jun. 16, 2011

Related U.S. Application Data

(63) Continuation-in-part of application No. 12/963,370, filed on Dec. 8, 2010.

(30) Foreign Application Priority Data

Dec. 10, 2009   (EP) ..................... 09075545

(51) Int. Cl.
*H04N 7/18*     (2006.01)
*G06K 9/00*     (2006.01)
(Continued)

(52) U.S. Cl.
CPC ............ *G01N 25/72* (2013.01); *G01J 5/0003* (2013.01); *G01J 5/02* (2013.01); *G01J 5/025* (2013.01);
(Continued)

(58) Field of Classification Search
None
See application file for complete search history.

(56) References Cited

U.S. PATENT DOCUMENTS 3,968,368 A * 7/1976 Sager ............... B07C 5/126
250/340
4,064,534 A * 12/1977 Chen ................ B07C 5/126
250/559.22
(Continued)

FOREIGN PATENT DOCUMENTS

CA         1051538         3/1979
CA         2650963         11/2007
(Continued)

OTHER PUBLICATIONS

Chan, Dr. John: "Automated Inspection and Container Monitoring at the Hot End." International Glass Review, Contract Communications, London, GB, Jan. 1, 1997, pp. 109-111, XP002991197. ISSN: 1359-4974 * the whole document *.
(Continued)

*Primary Examiner* — Chikaodili E Anyikire
*Assistant Examiner* — Kaitlin A Retallick
(74) *Attorney, Agent, or Firm* — Reinhart Boerner Van Deuren P.C.

(57) ABSTRACT

A system and method are disclosed for monitoring hot glass containers at the hot end as they stream from an I.S. machine manufacturing them to enable their quality to be monitored, enhanced, and controlled. The system monitors radiation from the hot glass containers, extracts images of each hot glass container, analyzes the images of the hot glass containers, and provides the images of the hot glass containers together with information indicative of the quality thereof to a display screen viewable by an operator to enable the quick identification of glass forming process deviations and to occasion continuous improvements in glass container quality. The system and method are independent of conditions and parameters that have hampered previously known attempts to monitor hot glass containers, and make possible
(Continued)

the production of glass containers of both high quality and substantially increased consistency.

42 Claims, 25 Drawing Sheets

(51) Int. Cl.
| | |
|---|---|
| *G01N 25/72* | (2006.01) |
| *G01J 5/00* | (2006.01) |
| *G01J 5/02* | (2006.01) |
| *G01J 5/06* | (2006.01) |
| *G01J 5/08* | (2006.01) |
| *G01N 33/38* | (2006.01) |

(52) U.S. Cl.
CPC ............ *G01J 5/061* (2013.01); *G01J 5/0846* (2013.01); *G01N 33/386* (2013.01); *G01J 2005/0077* (2013.01)

(56) References Cited

U.S. PATENT DOCUMENTS

| | | | |
|---|---|---|---|
| 4,492,476 A | 1/1985 | Miyazawa | |
| 5,032,727 A | 7/1991 | Cox et al. | |
| 5,345,389 A | 9/1994 | Calvin et al. | |
| 5,583,337 A * | 12/1996 | Chan ................. | B07C 5/126 250/330 |
| 5,926,556 A * | 7/1999 | Douglas ............ | G06K 7/10722 250/223 B |
| 6,049,379 A * | 4/2000 | Lucas ................ | G01N 21/9036 250/223 B |
| 6,188,079 B1 | 2/2001 | Juvinall et al. | |
| 6,212,962 B1 * | 4/2001 | Lucas ................ | B07C 5/3408 73/865.8 |
| 6,584,805 B1 * | 7/2003 | Burns ................ | C03B 9/41 209/524 |
| 6,822,970 B1 * | 11/2004 | Redd ................ | C03B 9/41 370/445 |
| 6,894,775 B1 * | 5/2005 | Cech ................ | G01N 21/90 356/239.1 |
| 7,006,937 B2 | 2/2006 | Huntley | |
| 7,054,710 B2 | 5/2006 | Hartmann et al. | |
| 7,256,389 B2 * | 8/2007 | Prasad ................ | G01N 21/90 250/223 B |
| 2003/0155281 A1 * | 8/2003 | Welker ................ | G01N 21/90 209/524 |
| 2004/0262523 A1 * | 12/2004 | Bathelet ................ | G01N 25/72 250/349 |
| 2005/0288881 A1 * | 12/2005 | Hori ................ | G01D 1/14 702/82 |
| 2006/0096319 A1 * | 5/2006 | Dalstra ................ | G01N 33/386 65/29.11 |
| 2006/0262971 A1 * | 11/2006 | Foes ................ | G01N 25/72 382/141 |
| 2007/0102628 A1 | 5/2007 | Prasad | |
| 2009/0028417 A1 * | 1/2009 | Floeder ................ | B65H 26/00 382/141 |
| 2010/0009356 A1 | 1/2010 | Snider et al. | |
| 2010/0067780 A1 * | 3/2010 | Kawaragi ............ | B81C 99/005 382/149 |
| 2012/0211331 A1 * | 8/2012 | Simon ................ | C03B 9/41 198/572 |
| 2012/0226378 A1 * | 9/2012 | Simon ............. | G05B 19/41875 700/157 |

FOREIGN PATENT DOCUMENTS

| | | |
|---|---|---|
| EP | 0679883 A2 | 2/1995 |
| EP | 0 643 297 B1 | 12/2002 |
| EP | 1494012 A1 | 1/2005 |
| EP | 2482078 | 1/2012 |
| GB | 1523366 | 8/1978 |
| GB | 2149910 A | 6/1985 |
| JP | S51-112818 | 10/1976 |
| JP | H3-15986 | 1/1991 |
| JP | H5-142172 | 6/1993 |
| JP | H8-43322 | 2/1996 |
| JP | 2001-272209 | 10/2001 |
| JP | 20030083718 A | 3/2003 |
| JP | 2005-315466 | 11/2005 |
| JP | 2007-33250 | 2/2007 |
| JP | 2008-501188 | 1/2008 |
| JP | 2009-535649 | 10/2009 |
| WO | 0056673 A1 | 9/2000 |
| WO | 2004011935 A1 | 2/2004 |
| WO | 2005119565 | 12/2005 |
| WO | 2007130962 | 11/2007 |

OTHER PUBLICATIONS

Micheletti, Roberto.: "Automatic Visual Inspection for Glass Production." ISMCR. Proceedings of the International Symposium on Measurement and Control in Robotics, XX, XX, Jan. 1, 1998, pp. 127-131, XP009069952 * abstract; section "3. Algorithm implementation" *.
English language translation of Japanese Office Action for Japanese Application No. 2010-275551 provided by foreign associate on May 23, 2014, 6 pages.
Partial English language translation of Japanese reference H3-15986 provided by foreign associate on May 23, 2014, 2 pages.
Partial English language translation of Japanese reference H5-142172 provided by foreign associate on May 23, 2014, 1 page.
English language translation of Japanese reference 2007-33250 provided by foreign associate on May 23, 2014, 18 pages.
Partial English language translation of Japanese reference 2001-272209 provided by foreign associate on May 23, 2014, 3 pages.
English language translation of Japanese reference 2005-315466 provided by foreign associate on May 23, 2014, 8 pages.

\* cited by examiner

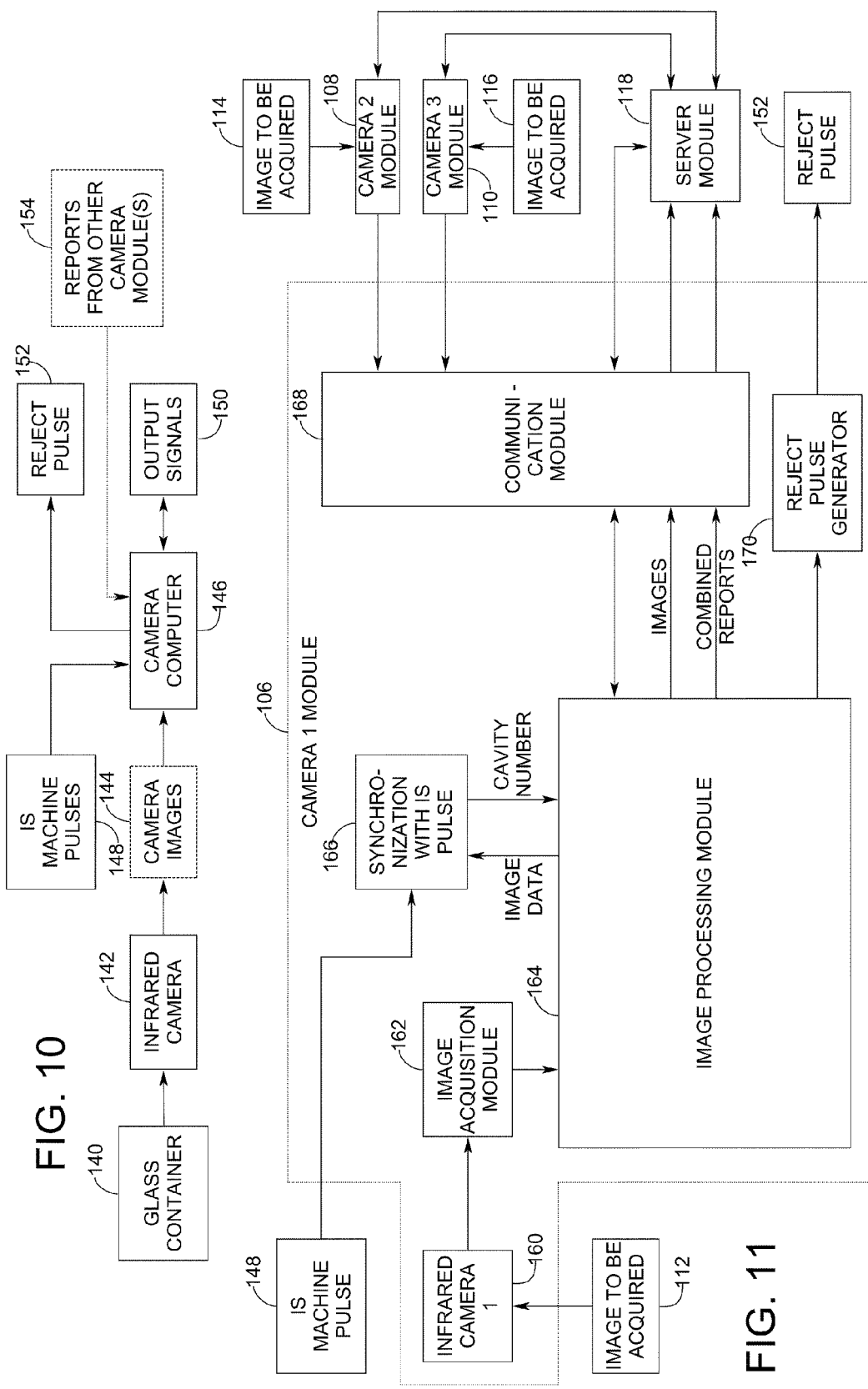

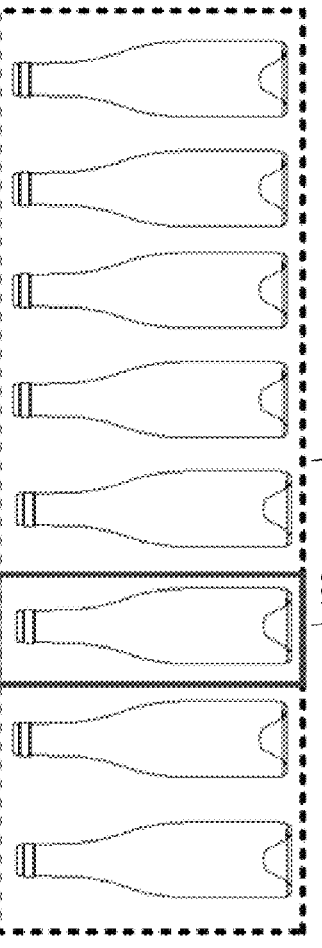
FIG. 13
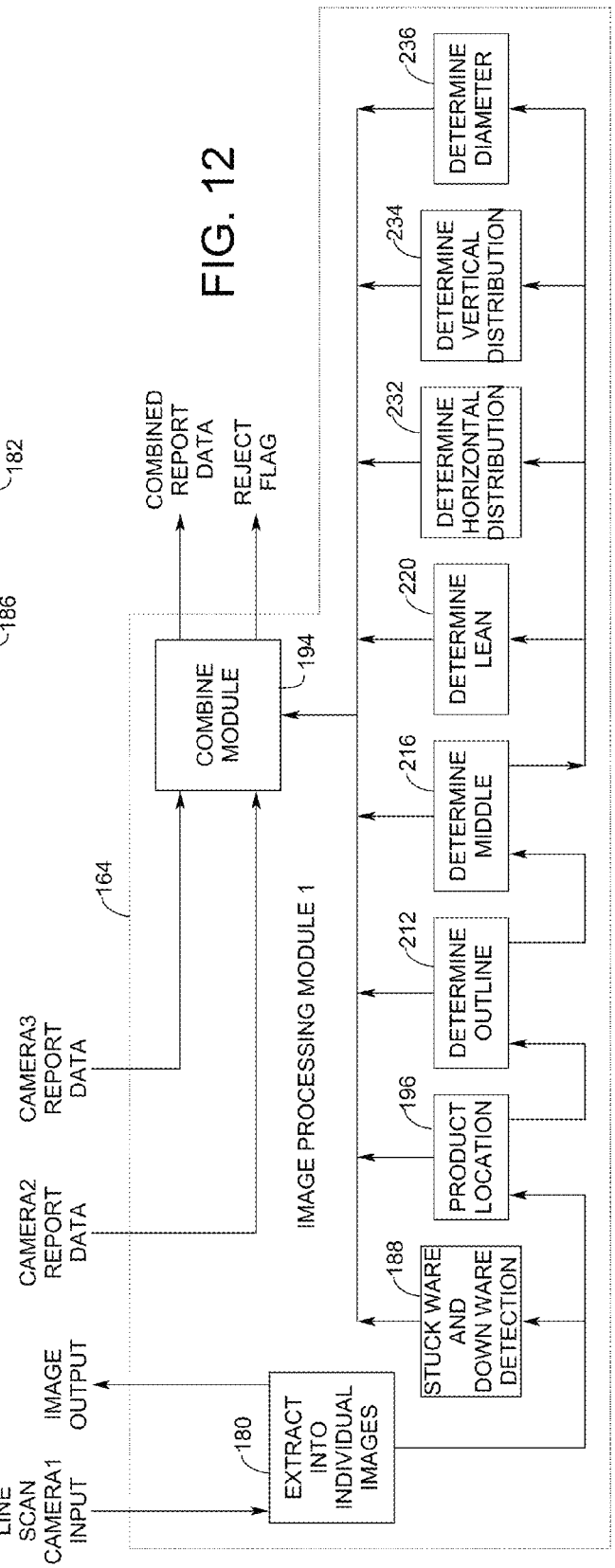
FIG. 14
FIG. 12

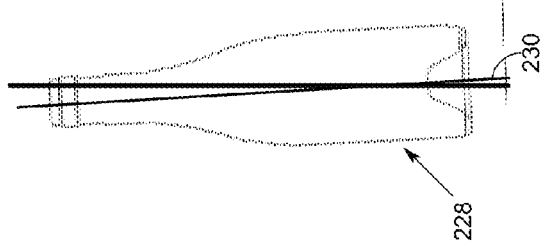
FIG. 15  FIG. 18  FIG. 19  FIG. 20  FIG. 21
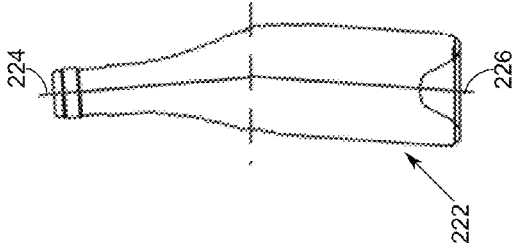
FIG. 17
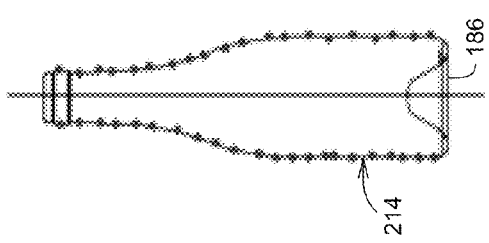
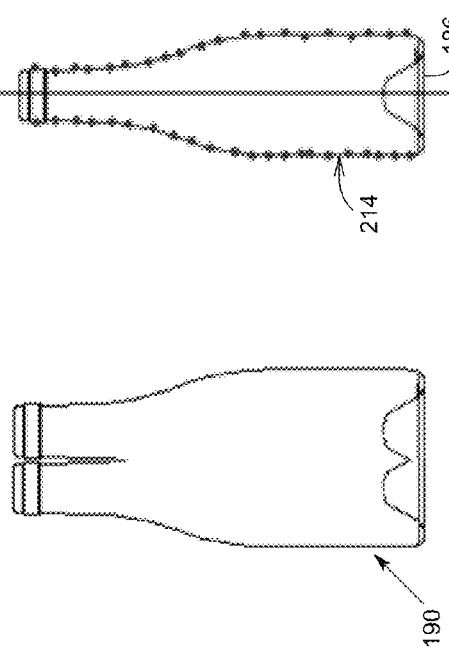
FIG. 16
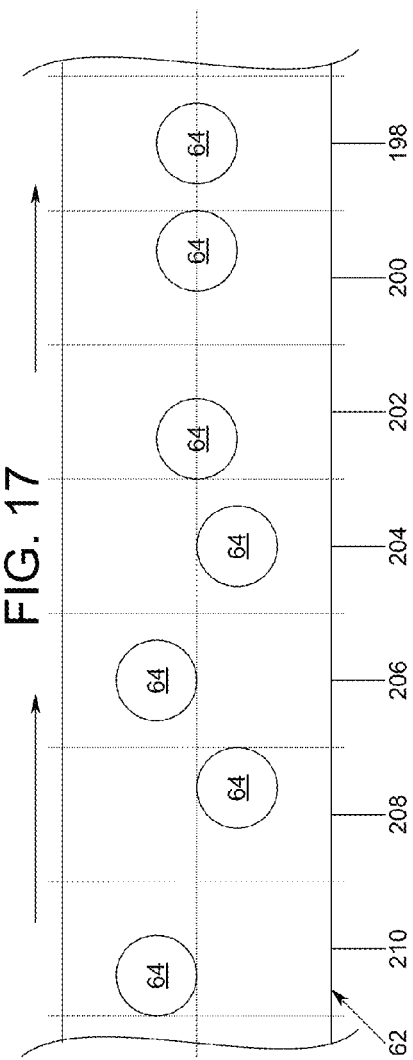
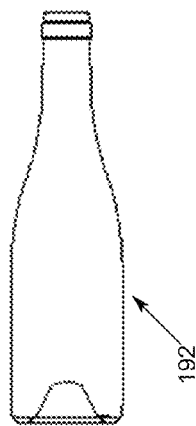

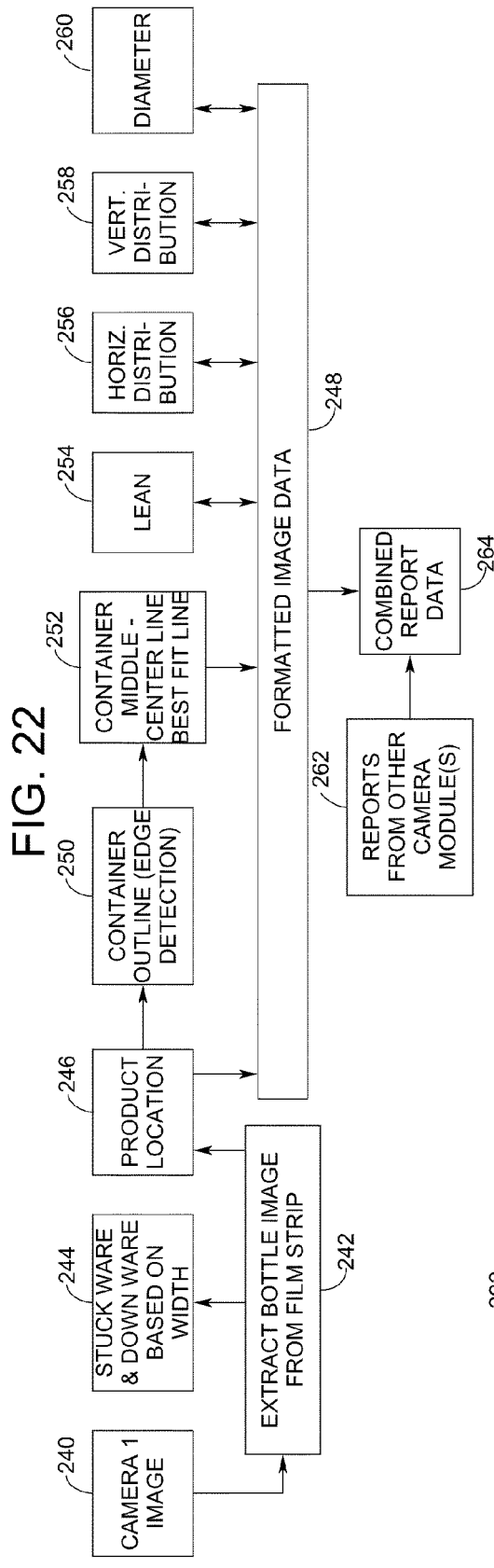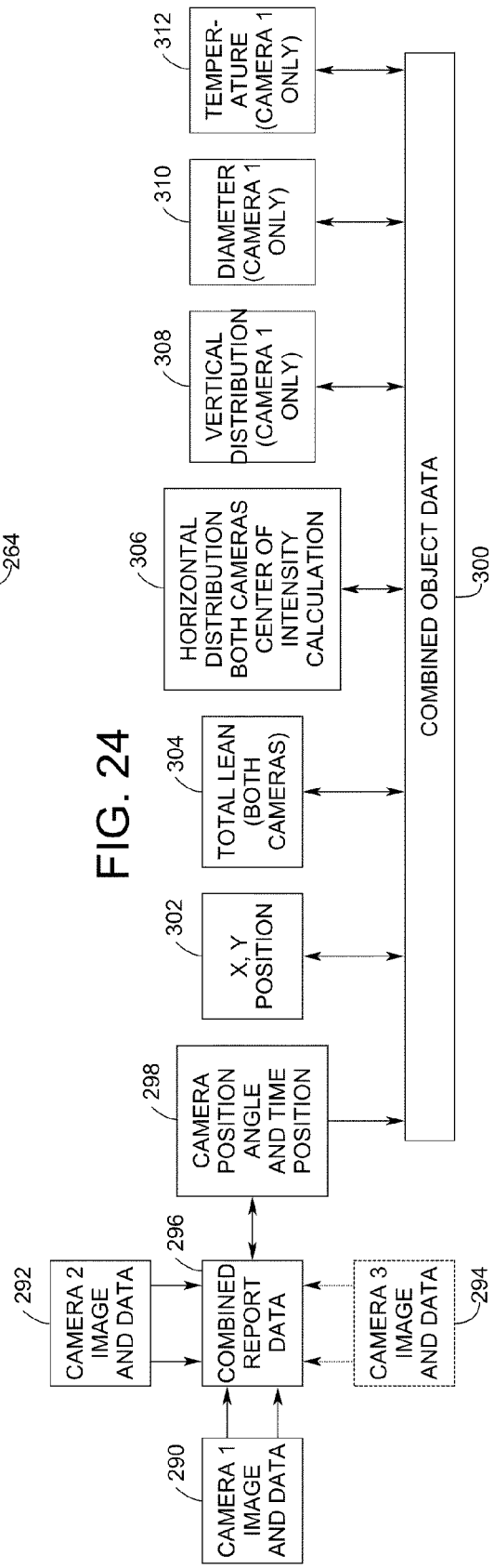

SYSTEM AND METHOD FOR MONITORING HOT GLASS CONTAINERS TO ENHANCE THEIR QUALITY AND CONTROL THE FORMING PROCESS

CROSS REFERENCE TO RELATED APPLICATIONS

This patent application is a continuation-in-part of U.S. patent application Ser. No. 12/963,370, filed on Dec. 8, 2010, entitled "Method and System for Monitoring and Controlling a Glass Container Forming Process," which patent application claims priority benefit under 35 U.S.C. §119(a) from European Patent Application No. EP 09075545.5 filed in the European Patent Office on Dec. 10, 2009, both of which are assigned to the assignee of the present patent application, and both of which are hereby incorporated herein by reference.

BACKGROUND OF THE INVENTION

Field of the Invention

The present invention relates generally to a system and method for monitoring hot glass containers at the hot end as they stream from an I.S. machine manufacturing them to enable their quality to be monitored, enhanced, and controlled.

Glass containers are made in a manufacturing process that has three parts, namely the batch house, the hot end, and the cold end. The batch house is where the raw materials for glass (typically including sand, soda ash, limestone, cullet (crushed, recycled glass), and other raw materials) are prepared and mixed into batches. The hot end begins with a furnace, in which the batched materials are melted into molten glass, and from which a stream of molten glass flows.

The molten glass is cut into cylinders of glass called gobs, which fall by gravity into blank molds. In the blank molds, a pre-container referred to as a parison is formed, either by using a metal plunger to push the glass into the blank mold, or by blowing the glass from below into the blank mold. The parison is inverted and transferred to a mold, where the parison is blown out into the shape of the container. The hot end also includes an annealing process which prevents the containers from having weakened glass caused by stresses caused by uneven cooling. The annealing process is used to achieve even cooling, using an annealing oven or Lehr to heat the containers, and then slowly cool them over a twenty to sixty minute period.

The equipment at the cold end of the glass container manufacturing process inspects the containers to ensure that they are of acceptable quality. All glass containers are inspected by automated machines after manufacturing for a variety of faults. Those skilled in the art will appreciate that if there is a problem in the way that glass containers are being molded by the I.S. machine, unless that problem is readily apparent from a casual inspection of the glass containers as they stream from the I.S. machine on conveyors that take them from the I.S. machine, through the annealing oven or Lehr, and through the inspection equipment at the cold end, there may be thousands of defective glass containers that require scrapping by the time that the existence of a problem is first determined.

Accordingly, it is beneficial to determine the existence of a recurring quality issue in glass containers as close as possible to the time that they exit the I.S. machine and while they are still very hot. Several attempts to inspect hot glass containers at the hot end of the glass container manufacturing line have been made. An early attempt is illustrated in U.S. Pat. No. 5,583,337, granted on Dec. 10, 1996, to Chan, which used a camera sensitive to infrared radiation located opposite the travel of the hot glass container through an inspection zone. The image of each hot glass container was processed into regions and data for each region was compared to predetermined parameters in order to determine whether or not the hot glass container was defective.

Another early attempt is illustrated in European Patent No. 643,297, granted on Dec. 18, 2002, to Troost, which used one or two infrared cameras and compared infrared energy distribution and/or energy differences in images from the infrared camera with a mathematical reference model that had been developed by means of specific physical properties, such as the released (emitted) infrared radiation in combination with specific sizes and glass composition of the product.

Another attempt is illustrated in U.S. Pat. No. 6,188,079, granted on Feb. 13, 2001, to Juvinall et al., which measured the intensity of radiation emitted by hot glass containers at two different wavelengths, namely a near-infrared wavelength where the image varied as a function of both surface temperature and wall thickness, and a higher wavelength infrared wavelength where the image varied as a function of surface temperature only. Wall thickness was determined by comparing the images with each other.

A more recent attempt is illustrated in U.S. Patent Application Publication No. 2006/0096319, published on May 11, 2006, to Dalstra, which uses near-infrared wavelength radiation from hot glass containers to obtain an image of the hot glass containers. Each image is subdivided into at least two regions, average intensity values for the regions for each hot glass container image are determined, and the average intensity value of each region for each hot glass container is compared with a reference value such as "the running average" to determine deviations therefrom, from which an error signal may be generated. Additionally, a cooling curve is calculated and used as a reference to compensate for the difference in the amount of radiation of glass products due to different cooling times.

U.S. Pat. No. 5,583,337, European Patent No. 643,297, U.S. Pat. No. 6,188,079, and U.S. Patent Application Publication No. 2006/0096319 are each incorporated herein by reference in their entirety.

All of these systems may generate error signals even when there is a change in the amount of infrared radiation that is not brought about due to a change in the forming process, but is due instead to changes in environmental and other conditions and parameters, such as, for example, the ambient temperature, the ambient humidity, the cooling air temperature, the cooling air humidity, smoke and dirt in the air, the infrared camera settings, contamination of the infrared camera optics, the production speed, the glass material composition, and glass container weight. These conditions and parameters, which as such have nothing to do with glass container quality, can drastically alter the measured infrared radiation intensities depending on, for example, whether the system is operating at day or night, differences occasioned by different seasons, the production location, and/or the I.S. machine itself.

Consequently, the operator must always be present to monitor the measurement results and the generated error signals carefully, to check the conditions and parameters, and to adjust reference values in order to compensate for continuously changing conditions and parameters. From a practical standpoint, this is highly undesirable, since labor costs are relatively high and the glass container manufacturing process occurs in a hot and noisy environment, which is not a favorable labor environment.

Another disadvantage of the known systems, and particular the Troost and Dalstra systems, is that when starting up the production of a glass container that has been produced earlier, the above mentioned conditions and parameters may have been changed, in which case the reference values and/or cooling curves used for the previous production may not be useful for the current production (and, if used, may actually produce glass containers that are of an unacceptable quality). For these systems, each time a new master reference and/or a new cooling curve is required, the startup time will be lengthened considerably, which is not desirable.

The inventors of the present invention in their previous European Patent Application No. EP 09075545.5, filed on Dec. 10, 2009, and assigned to the assignee of the present patent application, presented a substantial improvement to the systems that were mentioned above. That invention obtained infrared images of hot glass containers having a predetermined number of horizontal scan image lines with each pixel on each image line having a digital value. A value for the line radiation measurement for each image line was determined by summing the digital values of all of the pixels in each image line. A total radiation measurement for each hot glass container was obtained by summing the digital values of all of the pixels in all of the image lines for the hot glass container. By dividing each of the line radiation measurements by the total radiation measurement, the values for each glass container were normalized without the necessity of comparing them to an average value, a master reference value, or a cooling curve.

While this invention represents a tremendous advancement over the other systems that were mentioned above, further enhancements that have been made will be described hereinbelow. These further advancements will be directed to presenting images to an operator on a touchscreen user interface module that will enable the quick identification of glass forming process deviations including the geometry of the glass containers and the distribution of glass in the glass containers, provide forming process quality feedback, identify instant and formerly "unseen" potential improvements, provide early and adequate warnings of quality issues, and to occasion continuous improvements in glass container quality.

SUMMARY OF THE INVENTION

The disadvantages and limitations of the background art discussed above are overcome by the present invention. With this invention, a system and a method are provided for monitoring a glass container forming process at the hot end that is independent of the mentioned conditions and parameters that have hampered previously known attempts to monitor hot glass containers and with which it is possible to produce glass containers of both a high quality and a substantially increased level of consistency. The system monitors radiation from the hot glass containers, extracts images of each hot glass container, analyzes the images of the hot glass containers, and provides the images of the hot glass containers together with information indicative of the quality thereof to a display screen viewable by an operator.

One or more Short Wave Infrared ("SWIR") imaging device are positioned directly after the I.S. machine on opposing sides of the container to monitor hot glass containers as they are formed by the I.S. machine and pass by the SWIR imaging device(s) on the conveyor. The SWIR imaging device(s) provide electronic images from which an electronic image for each hot glass container is extracted. The electronic images of the hot glass containers are then processed to identify cavities that stand out from the overall population of all cavities using a number of different criteria that are relevant to the quality of the hot glass containers. In a preferred embodiment, at least some of the information coming from the hot glass containers may be normalized using the techniques taught in European Patent Application No. EP 09075545.5 filed in the European Patent Office on Dec. 10, 2009, which is assigned to the assignee of the present patent application. This normalizes the measurement from hot glass container to hot glass container and thereby removes the effects of overall temperature variations between glass containers, changing ambient conditions, and other variations affecting the measurements, which provides a unique quality reference for each glass container.

The processing performed on the images of the hot glass containers provides a wide variety of information regarding the hot glass containers to quickly identify deviations in the glass forming process and glass distribution throughout the hot glass containers. The images produced by the SWIR imaging devices are processed to identify cavities that stand out from the overall population of all cavities. The deviations used to identify the outliers are based upon the containers vertical and horizontal glass distribution, dimensional outline including lean, and the position on the conveyor. Cavities or sections producing outlying containers are quickly identified and visually displayed to the machine operator.

Some of this information is stored by the hot glass container quality analytical system in databases. Both the images of the hot glass containers and the analyses of the hot glass containers are presented on a user interface screen. In the preferred embodiment, the user interface screen is a touchscreen that allows a user to interact with the images and obtain analytical information presented with the images.

One of the features provided on the user interface screen is live views of the hot glass containers that are updated in real time. In a preferred embodiment, all the hot glass containers from all of the molds in all of the sections of the I.S. machine may be viewed simultaneously in real time. The hot glass container quality analytical system also displays annotations indicative of characteristics that are problematic, including displaying alarms and indications that containers are being rejected by the system. In one embodiment, the worst molds may be displayed to the user of the system to allow diagnosis and correction of the performance issues.

The Screens also include displays of vertical glass distribution and horizontal glass distribution, and in one preferred embodiment both vertical glass distribution and horizontal glass distribution are displayed simultaneously in a single display. This display is also presented in real time. In another preferred embodiment, the analytical information derived from the hot glass containers may be provided to the I.S. machine to enable automatic correction of some aspects of the glass container manufacturing process, including placement of the glass containers on the conveyor.

The hot glass container quality analytical system of the present invention thus presents images together with analytical information regarding the quality of the hot glass containers to an operator on a touchscreen display that enables the quick identification of glass forming process deviations including the geometry of the glass containers, the distribution of glass in the glass containers, and the positions of the glass containers on the conveyor. Forming process quality feedback is also provided, thereby identifying instant and formerly "unseen" potential improvements, providing early and adequate warnings of quality issues, and contributing to continuous improvements in glass container quality.

DESCRIPTION OF THE DRAWINGS

These and other advantages of the present invention are best understood with reference to the drawings, in which:

FIG. 10 is a schematic depiction illustrating the operation of one of the camera modules illustrated in FIG. 9 at a high level;

FIG. 11 is a schematic depiction showing the operation of the first camera module illustrated in FIG. 9 at a more detailed level than the level illustrated in FIG. 10;

FIG. 12 is a functional schematic depiction of the image processing module illustrated in FIG. 11;

FIG. 13 is a schematic drawing of a plurality of hot glass containers in a continuing digital "filmstrip" of images showing an image of a single hot glass container to be extracted from the "filmstrip" of images by the image processing module functionally illustrated in FIG. 12;

FIG. 14 is a is a schematic drawing of a hot glass container extracted from the image of a single hot glass container in the "filmstrip" of images illustrated in FIG. 13;

FIG. 15 is a side view of a "stuck ware" in which two still-plastic glass containers have become stuck together;

FIG. 16 is a side view of a "down ware" in which a glass container has fallen down on the conveyor;

FIG. 17 is a schematic top plan view of a portion of the conveyor showing longitudinal and lateral locations of each of a plurality of glass containers in a corresponding plurality of longitudinal locations;

FIG. 18 is a schematic drawing of the border detection occurring to the image of the single hot glass container image extracted from the "filmstrip" of images in FIG. 14;

FIG. 19 is a side view of glass container showing a line extending through a determined middle of the glass container;

FIG. 20 is a side view of a glass container that is a "leaner," with the determination of lean for the glass container being illustrated by lines illustrating lean for the top and bottom halves of the glass container;

FIG. 21 is a side view of another glass container that is a "leaner," with a single line illustrating lean for the glass container;

FIG. 22 is a schematic depiction showing the formatted image data flow occurring in the image processing module illustrated in FIGS. 10 and 12;

FIG. 24 is a schematic depiction showing the combination of object data that will be provided to the user interface modules and displayed thereupon;

DETAILED DESCRIPTION OF THE EXEMPLARY EMBODIMENT

Figure 1:
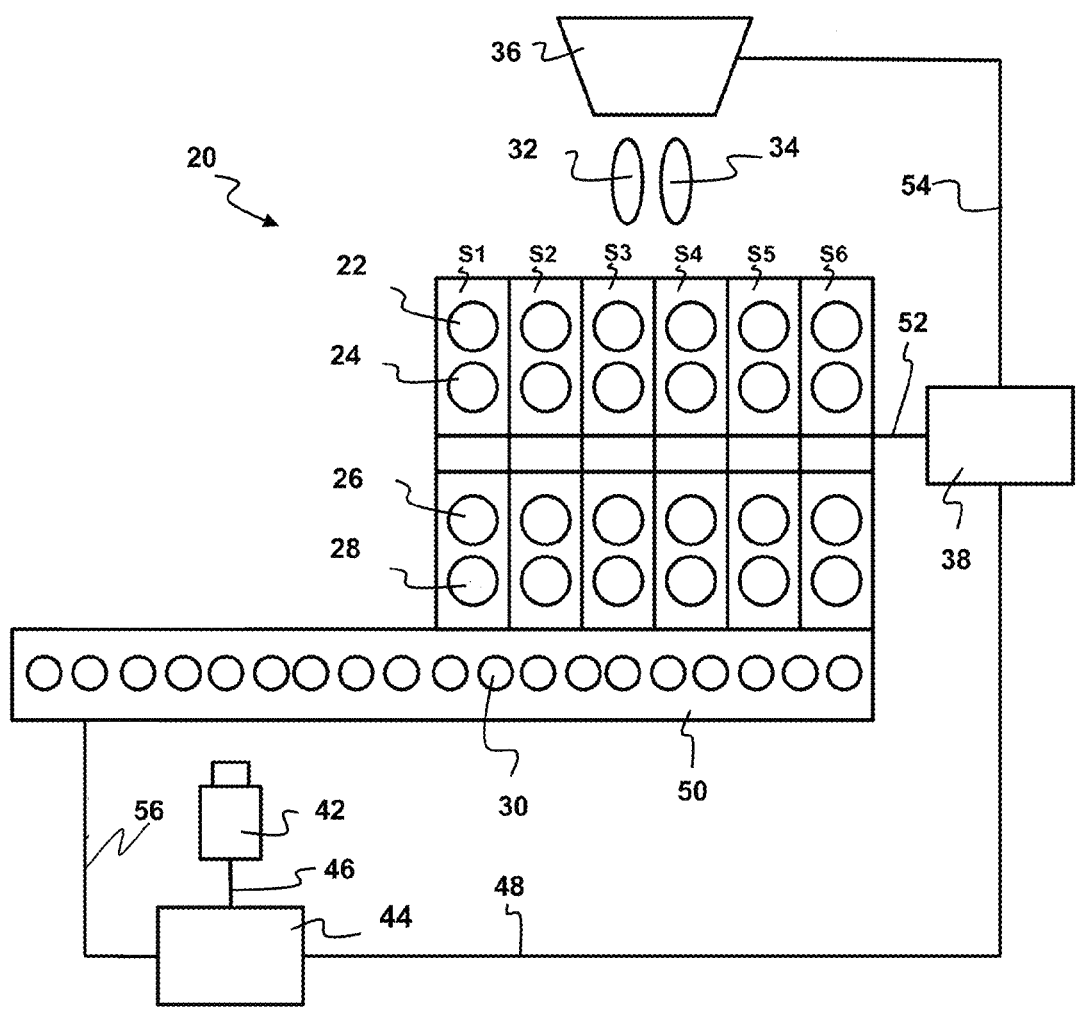
FIG. 1 is a schematic view of a forming machine and an embodiment of the analytical system.

FIG. 1 shows an embodiment of the system where the glass container forming machine 20 contains six independent sections S1, S2, . . . S6, each of which contains two forming stations 22 and 24. In one production cycle, the forming machine 20 produces twelve glass containers 30. Two molten glass gobs 32 and 34 are formed at the same moment by the feeder unit 36 and are loaded into the so-called blank moulds 22 and 24. Each section S1, S2, . . . S6 of the forming machine 20 in this embodiment contains two blank molds 22 and 24 in which pre-containers or parisons are formed by pressing or blowing depending on the process type (press-blow or blow-blow). The formed parisons are transferred to the so-called blow molds 26 and 28 where the parisons are blown into the final shape of the glass containers 30. The mechanisms of the forming machine 20 and the feeder unit 36 are controlled by the control unit 38 through lines 52 and 54, respectively.

The glass containers 30 are transported by a conveyor belt 50 through a measurement unit 42 which takes images of the hot glass containers 30 and sends these images to a processor unit 44 through a line 46. Although in this embodiment one measurement unit 42 is used, the number of measurement units 42 may be increased depending on the circumstances and the accuracy to be achieved. However, even with one measurement unit, the achieved accuracy is fairly high.

The measurement unit 42, an area camera in this embodiment, is preferably sensitive to Short Wave Infrared ("SWIR") radiation. Since radiation at wavelengths smaller than 3.0 microns from container glass is indicative of both the glass temperature and the glass thickness, a more accurate measurement may be obtained at wavelengths smaller than 3.0 microns, especially when analyzing relatively thicker glass containers. Therefore, a preferred embodiment of analytical system according to the present invention is that the measurement unit is sensitive to wavelengths of between 0.7 and 3.0 microns. More specifically, the measurement unit uses a Short Wave Infrared ("SWIR") camera, for example a 512 or 1024 pixels line-scan or area SWIR camera. The image taken by the camera of the hot glass container 30 shown in FIG. 2 may, for example, contain 512 image-lines, with each image-line for example containing 200 pixels.

Figure 2:
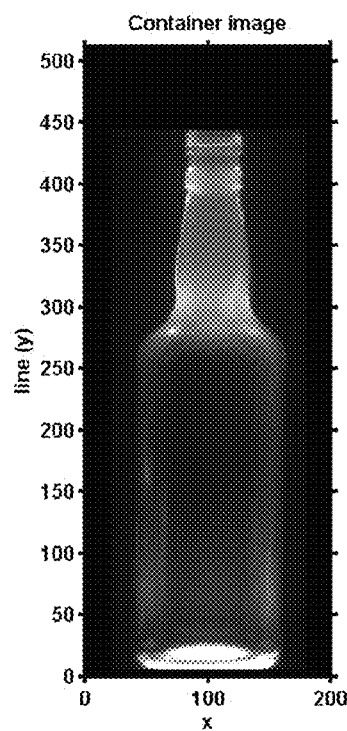
FIG. 2 is a an image of a glass container.
Figure 3:
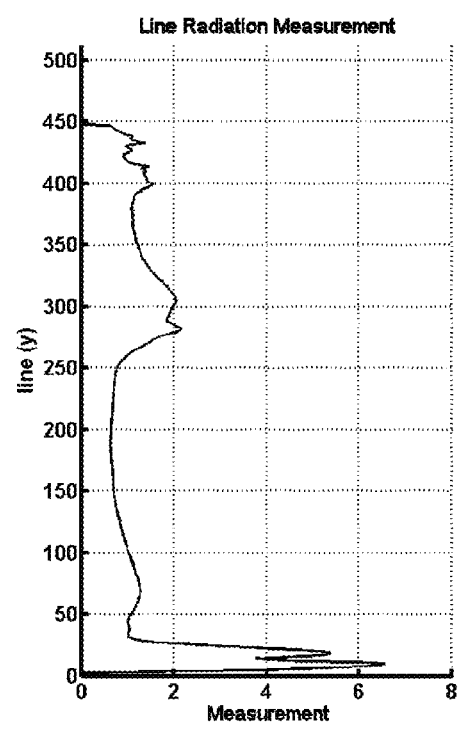
FIG. 3 is a line radiation measurement for the glass container shown in FIG. 1.

The processor unit 44 determines for each glass container 30 the total radiation measurement by summing the digital values of all the pixels in the glass container image. The total radiation measurement of the glass container shown in FIG. 2 has a value of 553. Next, the processor unit 44 determines the line radiation measurements by summing for each image-line the digital values of all 200 pixels. The line radiation measurements belonging to the glass container image of FIG. 2 are shown in FIG. 3. Next, the processor unit 44, determines the measurement-ratio curve by dividing the line radiation measurements by the total radiation measurement, as shown hereunder:

$$I_{tot,s} = \Sigma I_{x,y,s} (x=1,2, \ldots 200, y=1,2, \ldots, 512)$$

$$I_{y,s} = \Sigma I_{x,y,s} (x=1,2, \ldots 200)$$

$$I_{ratio,y,s} = (I_{y,s}/I_{tot,s})*100\%$$

Where:
$I_{tot,s}$=the total radiation measurement value of a glass container image, originating from station s;
$I_{x,y,s}$=the digital value of pixel x, y of the glass container image, originating from station s with y representing an image-line containing 200 x pixels, x=1 . . . 200, y=1 . . . 512, s=1 . . . 12;
$I_{y,s}$=the line radiation measurement value for image-line (y) of a glass container image, originating from station s; and
$I_{ratio,y,s}$=the measurement-ratio value for image-line y of a glass container image, originating from station s.

Figure 4:
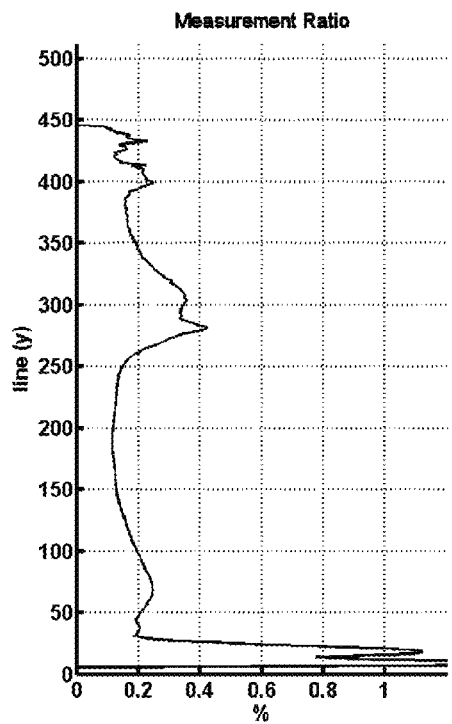
FIG. 4 is a measurement-ratio curve for the glass container shown in FIG. 2.

The measurement-ratio values are expressed in percentages for clarity. The measurement-ratio curve depicted in FIG. 4 belongs to the glass container shown in FIG. 2. The order in which these steps occur can be varied as long as the same results are achieved. One can easily see that, for example, an attenuation ● of the radiation received from the glass container 30 caused by an ambient parameter (for example smoke in the air) has no influence on the measurement-ratio curve:

$$I_{ration,y,s} = (\alpha I_{y,s}/\alpha I_{tot,s})*100\% = (I_{y,s}/I_{tot,s})*100\%$$

Next, the processor unit 44 determines a reference curve by averaging measurement-ratio curves from a number of glass containers 30 from all or certain selected forming stations. In a preferred embodiment, rather than using an average, the median value may instead be used. This reference curve is unique for the glass container type produced.

The values of the reference curve are derived as illustrated below:

$$I_{reference,y} = \left(\sum_{k=1}^{N} I_{ratio,y,k}\right) / N$$

Where:
$I_{reference,y}$=the reference curve value for line (y); and
N=the number of glass containers 30 taken into account.

Figure 5:
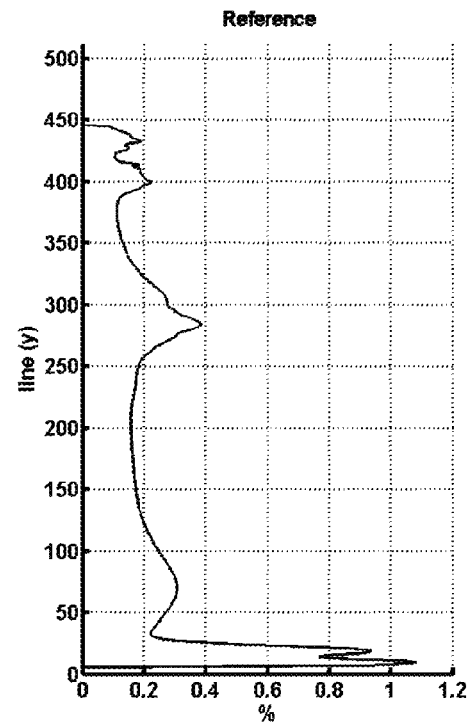
FIG. 5 is a reference curve for the glass container shown in FIG. 2.
Figure 6:
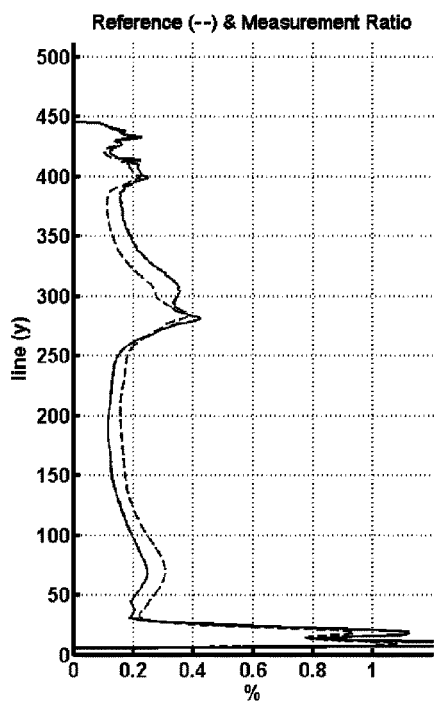
FIG. 6 is the reference curve together with the measurement-ratio curve for the glass container shown in FIG. 2.

The reference curve may be stored and used later to decrease the time necessary to start up the production of the particular glass container 30 on the same or on another forming machine. The reference curve belonging to the glass container type in this example is shown in FIG. 5. In FIG. 6, the reference curve is shown together with the measurement-ratio curve of FIG. 4.

The processor unit 44 next determines the relative difference curve by subtracting the reference curve from the measurement-ratio curve and dividing the difference by the reference curve. This is illustrated hereunder:

$$\Delta I_{s,y} = ((I_{ratio,s} - I_{reference,y})/I_{reference,y})*100\%$$

Where:
$\Delta I_{s,y}$=the relative difference value at line y of a glass container image originating from the station s.

Figure 7:
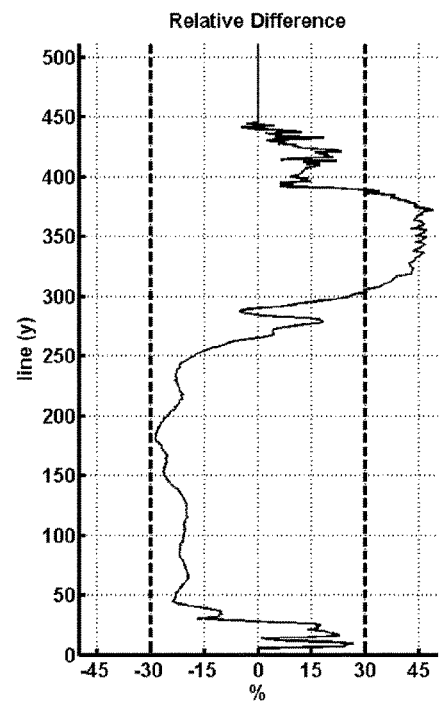
FIG. 7 is a relative difference curve for the glass container shown in FIG. 2.

The relative difference curve shows how much and where the measurement-ratio curve of a glass container deviates from the reference curve. The processor unit 44 may display on a connected monitor (not shown) for each forming station the relative difference curve in order to show the quality of the glass containers produced at the forming station. In FIG. 7, the relative difference curve is shown for the glass container of FIG. 2 with the corresponding measurement-ratio curve shown in FIG. 4.

In this specific example the relative difference curve in FIG. 7 shows a positive deviation in the upper part of the glass container and a negative deviation in the lower part of the glass container, indicating too much glass in the upper part of the glass container and too little glass in the lower part of the glass container. The relative difference curve will be close to zero at every point for high quality glass containers.

Subsequently, the processor unit (44) compares the relative difference curve with predetermined tolerance curves and generates an alarm signal if a relative difference value exceeds the corresponding tolerance value. This is illustrated hereunder:

Alarm if: $\Delta I_{s,y} < I_{T-,y}$ or $\Delta I_{s,y} > I_{T+,y}$

Where:
$I_{T-,y}$=the negative tolerance value for line y; and
$I_{T+,y}$=the positive tolerance value for line y.

The alarm signal may, for example, be used in order to reject glass containers which have an unacceptable quality on line 56 in FIG. 1. In FIG. 7 the negative tolerance values are set at −30% and the positive tolerance values are set at +30%. In FIG. 7 an alarm signal is generated because the relative difference values for line 300 through line 380 exceed the positive tolerance values.

In order to adjust the forming process automatically, the processor unit 44 may send the relative difference curve from each forming station to the control unit 38 over line 48. The control unit 38 adjusts the appropriate process parameters until the relative difference curve for each forming station is close to zero. This may be done without the need to have an operator monitoring the process continuously.

The processor unit 44 is synchronized with the forming machine 20 and with conveyor belt 50 in such a way that processor unit 44 knows from which forming station each glass container 30 originates.

Figure 8:
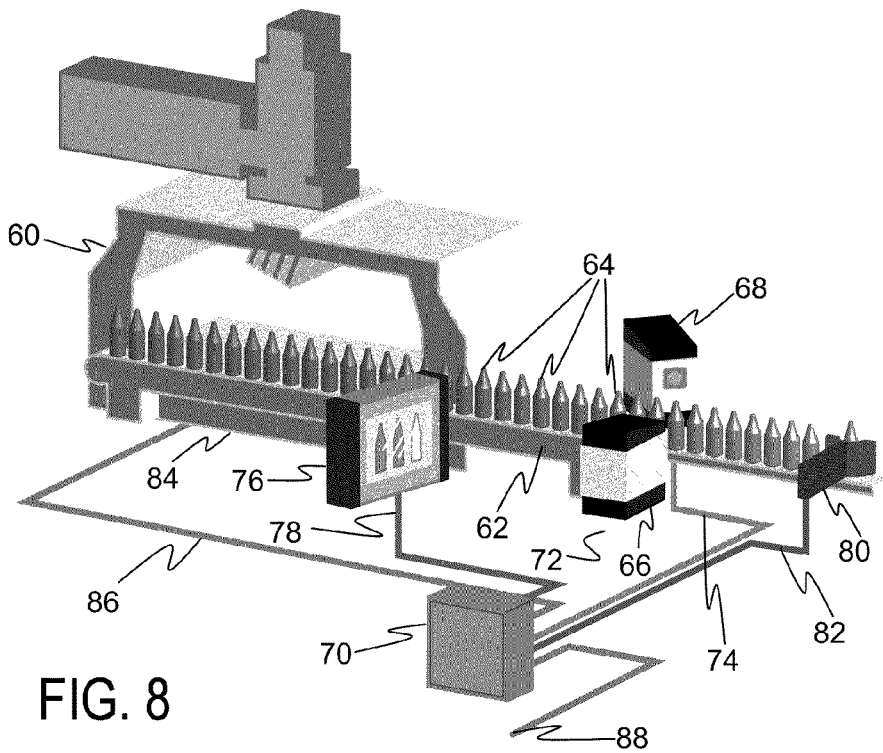
FIG. 8 is a simplified view of a hot glass container quality analytical system according to the present invention showing the essential components thereof as installed in a typical glass container manufacturing line.

Referring next to FIG. 8, the major components of the hot glass container quality analytical system of the present invention are illustrated in schematic fashion. An I.S. machine 60 has a conveyor 62 extending therefrom on which a stream of hot glass containers 64 are conveyed away from the I.S. machine 60. Two camera modules 66 and 68 are located in positions to monitor the hot glass containers 64 as they pass by the two camera modules 66 and 68 on the conveyor 62. In a preferred embodiment, the camera modules 66 and 68 each include a SWIR imaging acquisition device that scans a vertical line which will be used to acquire images of the hot glass containers 64 as they pass by on the conveyor 62. As the hot glass containers 64 pass by, a multiplicity of vertical lines will be scanned that will together form electronic images of the hot glass containers 64.

The first camera module 66 is located with an axis orthogonal to the longitudinal axis of the conveyor 62 on which the hot glass containers 64 travel after leaving the I.S. machine 60, with the conveyor 62 being oriented toward the side of the hot glass containers 64 passing by on the conveyor 62. The second camera module 68 is located with an axis at a predefined angle with respect to the longitudinal axis of the conveyor 62, with the conveyor 62 also being oriented toward the side of the hot glass containers 64 passing by on the conveyor 62. The camera modules 66 and 68 are preferably located such that their respective axes intersect at a point at the middle of the lateral axis of the conveyor 62, which is at the centerline of the conveyor the conveyor 62 (if they are not so located, appropriate mathematical compensation may be made). It should be noted that instead of the two camera modules 66 and 68 being used, either a single camera module 66 located as it is located in FIG. 8, or more than the two camera modules 66 and 68, could instead be used, although better overall results may be obtained through the use of more than a single camera module 66 being used.

The camera modules 66 and 68, which are the first of the major components of the hot glass container quality analytical system of the present invention, are connected to a control unit 70 that is used to operate the hot glass container quality analytical system of the present invention, which is the second of the major components of the hot glass container quality analytical system of the present invention. The camera module 66 is connected to the control unit 70 via a connection 72, and the camera module 68 is connected to the control unit 70 via a connection 74. The connections 70 and 72 may be network connections such as TCPIP network connections.

A user interface module 76, which is the third of the major components of the hot glass container quality analytical system of the present invention, is connected to the control unit 70 via a connection 78, which may be a network connection such as a TCPIP network connection. The user interface module 76 will be used both to display information generated by the hot glass container quality analytical system as well as to set up the hot glass container quality analytical system. Further, the information generated by the hot glass container quality analytical system and displayed on the user interface module 76 may be used to assess the quality of the hot glass containers 64 manufactured by the I.S. machine 60 as well as to control the operation of the I.S. machine 60 to improve the quality of the hot glass containers 64 manufactured by the I.S. machine 60.

Based upon the information generated by the hot glass container quality analytical system of the present invention, the hot glass containers 64 that are determined to be of unacceptable quality by the hot glass container quality analytical system are rejected and removed from the stream of the hot glass containers 64 on the conveyor 62. A glass container reject mechanism 80 that performs this function is operated by the control unit 70 via a connection 82, which may be a simple trigger signal such as a twenty-four Volt pulse.

The hot glass container quality analytical system of the present invention is provided with timing pulses by an I.S. machine control unit 84 via a connection 86. These timing pulses are used by the hot glass container quality analytical system to define from which section and which mold each of the hot glass containers 64 on the conveyor 62 originates. In this way, the hot glass container quality analytical system of the present invention can display this information to an operator accessing the user interface module 76. It is also contemplated that the information generated by the hot glass container quality analytical system of the present invention may be used to automatically control the I.S. machine 60 through the I.S. machine control unit 84 via the connection 86.

It may be noted that the control unit 70 of the hot glass container quality analytical system of the present invention is depicted as having another connection 88, the distal end of which is not shown as being connected in FIG. 8. This connection 88, which may also be a network connection such as a TCPIP network connection, may be used to connect additional remote control units (not shown in FIG. 8) which may be located, for example, in a control room at the glass container manufacturing plant at which the I.S. machine 60 is located, in an engineer's office either at that manufacturing plant or at another remote location, and/or in another remote location such as, for example, the hot glass container quality analytical system provider's facility to remotely monitor and troubleshoot the system at customer locations.

Figure 9:
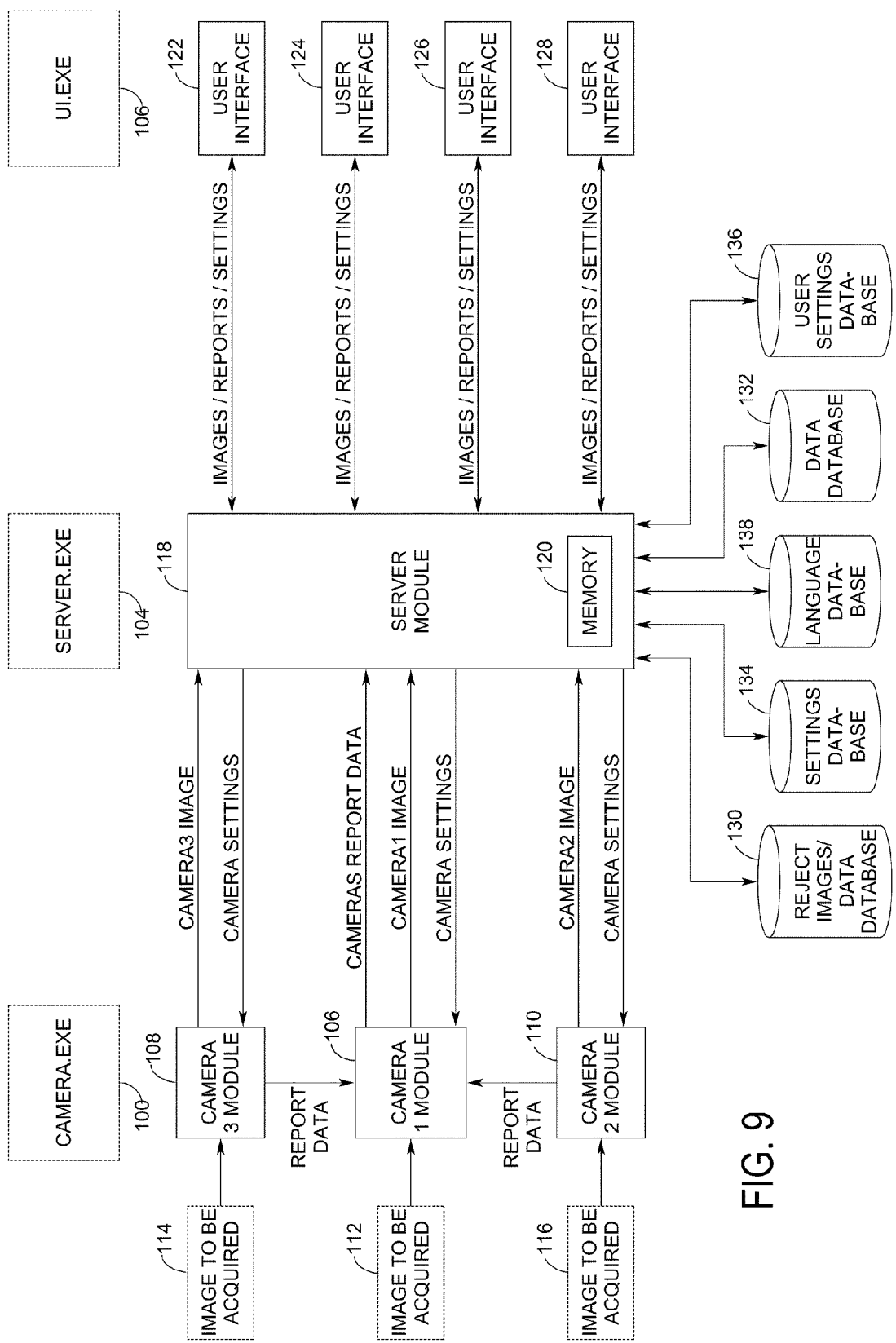
FIG. 9 is a schematic view showing the operational connections of the essential components of the exemplary hot glass container quality analytical system illustrated in FIG. 8 showing the flow of data between the components.

Referring next to FIG. 9, the operational connections of the essential elements of the exemplary hot glass container quality analytical system are shown in a manner that illustrates the flow of data between one or more camera modules, a server module, and one or more user interface modules. These three elements are networked together, typically by TCPIP network connections, which may be local or remote, or a combination of both local and remote. At a high level, the three essential components of the exemplary hot glass container quality analytical system that were referenced in FIG. 8 (the camera modules, the control unit, and the user interface module) are shown in an expanded fashion illustrating the implementation of three software executable modules, namely a camera software module 100, a server software module 102, and a user interface software module 104. These three executables may reside on separate computers, or, alternatively on the same computer. Alternately, the three software executable modules may be partially combined or fully combined into a single executable module.

In the implementation of FIG. 9, three camera modules 106, 108, and 110 are shown, of which it will be understood that first camera module 106 is the one that is mounted orthogonally to the conveyor (and which corresponds to the camera module 66 in FIG. 8). Thus, the first camera module 106 is used to acquire first images 112, the second camera module 108 is used to acquire second images 114, and the third camera module 110 is used to acquire third images 116 (all of which are obtained from different angles with respect to hot glass containers). It is entirely possible for the hot glass container quality analytical system of the present invention to accommodate inputs from at least four camera modules if desired.

The camera modules 106, 108, and 110 do calculations on the images 112, 114, and 116 respectively detected by an infrared camera contained in each of the camera modules 106, 108, and 110 and operating in a vertical line scanning manner as glass containers pass by the location of the infrared camera on the conveyor. The camera modules 106, 108, and 110 do calculations on the glass container images 112, 114, and 116, respectively, and each generates a glass container image report for each glass container image. The glass container image reports from the second camera module 108 and the third camera module 110 (if they are used) are provided to the first camera module 106, which is the main camera module, which consolidates the glass container image reports from the camera modules 106, 108, and 110 for each glass container.

The consolidated glass container image report is sent from the first camera module 106 to a server module 118, which contains memory 120. The memory 120 of the server module 118 is preferable at least sufficient to store all of the glass container reports for all glass containers monitored by the hot glass container quality analytical system of the present invention for the last hour. The images 112, 114, and 116 from the three camera modules 106, 108, and 110, respectively, are sent from the three camera modules 106, 108, and 110, respectively, to the server 118 (and these images 112, 114, and 116 pass from the camera modules 106, 108, and 110, respectively, through the server 118 to any of four user interface modules 122, 124, 126, and 128 if the user of these modules 122, 124, 126, and 128 wish to view them). Otherwise, the images 112, 114, and 116 are not sent from the camera modules 106, 108, and 110, respectively. The server 118 itself sends camera settings to each of the three camera modules 106, 108, and 110 to control the operation of the three camera modules 106, 108, and 110.

The user interface modules 122, 124, 126, and 128 are used to access the system and view screens presenting a wide array of information regarding the operation of the hot glass container quality analytical system, including live images, reports, and also screens allowing settings to be inputted into the hot glass container quality analytical system. Each of these user interface modules 122, 124, 126, and 128 is identical or essentially identical, with typical locations for the user modules 122, 124, 126, and 128 being on the plant floor, in a control room at the plant, in an engineer's office at the plant, and in remote locations such as the hot glass container quality analytical system provider's facility to remotely monitor and troubleshoot it at a customer's location. The user interface modules 122, 124, 126, and 128 typically include an interactive display such as a touchscreen or a mouse or trackpad interface in conjunction with a display screen.

The server module 118 also operates five different databases. The first of these databases is a rejected glass container images database 130, which in the preferred embodiment is used to contain images of at least the most recent 50,000 glass containers that have been rejected. The server module 118 calculates periodic averages for each cavity of the I.S. machine manufacturing the glass containers being analyzed. These periodic averages may be calculated as often as once each minute and as infrequently as once each 24 hours, with the preferred period being once every five minutes. These periodic averages for each cavity are stored in a second database, namely the glass container data database 132. Both the rejected glass container images database 130 and the glass container data database 132 may include time identifying data (the rejected glass container images database 130 includes the image of the rejected glass container, the time associated with each rejected glass container, and the reason that the glass container was rejected).

A third database, namely a parameter settings database 134, is used to store all of the parameters for a particular glass container, including camera settings, system settings, and limits for some parameters. A fourth database is a user settings database 136, which is used to control user interfaces through the user interface modules 122, 124, 126, and 128. The user settings database 136 may store preferred settings for each user for user passwords, user rights associated with each user, and language used by each user. A fifth database is a language database 138, which contains data needed to operate the user interfaces 122, 124, 126, and 128 in each of a plurality of languages useable with the hot glass container quality analytical system.

Referring next to FIG. 10, the operation of any of the camera modules illustrated in FIG. 9 is shown at a fairly high level. A glass container 140 is imaged by an infrared camera 142, which produces camera images 144 that are provided to a camera computer 146. As implemented in the preferred embodiment, the infrared camera 142 does not use a telecentric lens, which would have to be as large as the largest glass container to be viewed by the infrared camera 142 (since telecentric lenses collect rays in parallel rather than in the fashion of non-telecentric lenses). Thus, it will be appreciated that the distance of the infrared camera 142 from the glass containers is quite important in order for the system to operate properly.

The camera computer 146 extracts the image of each glass container 140 and also produces a glass container image report for each glass container 140. I.S. machine pulses 148 are provided to the camera computer 146, which is able to determine for each image of a glass container 140 in which section and mold the glass container it represents was manufactured. The camera computer 146 sends the glass container image report for each glass container image 140 together with the extracted images thereof as output signals 150 to the server module 118 (shown in FIG. 9). Alternately, if the camera module is an auxiliary camera module rather than the main camera module, it will send the glass container image report for each glass container 140 to the main camera module for consolidation into a combined glass container image report.

The infrared camera 142 also provides a reject pulse 152 for each glass container image 140 that it determines is of unacceptable quality. This reject pulse 152 is sent to the glass container reject mechanism 80 (shown in FIG. 8) to reject each unacceptable quality glass container. If the camera module is the main camera module, it will receive glass container image report(s) from one or more auxiliary camera modules 154 for each image of a glass container 140, which it will consolidate into a combined glass container image report that it sends to the server module 118.

Referring now to FIG. 11, the operation of the first camera module 106 illustrated in FIG. 9 is shown at a much more detailed level. The first images 112 are acquired by a first infrared camera 160 and provided to an image acquisition module 162 which receives the images of the stream of hot glass container 64 on the conveyor 62 (both shown in FIG. 8) and sends these continuous images to an image processing module 164 for further analysis. Each image will have a resolution of a number of horizontal lines and a number of vertical lines that is determined by the vertical resolution of the first infrared camera 160 and the scan frequency (the number of scans taken as the glass containers move along the conveyor 62 (also shown in FIG. 8). In one preferred embodiment, the resolution is 1024 horizontal lines and 1024 vertical lines.

The I.S. machine pulses 148 from the I.S. machine control unit 84 of the I.S. machine 60 (both shown in FIG. 8) are sent to a synchronization module 166 in the first camera module the first camera module 106, where they are used to time the cycle of the hot glass container quality analytical system. There is one I.S. machine pulse 148 per complete I.S. machine cycle (which includes the manufacture of one hot glass container 64 from each of the cavities in each of the sections of the I.S. machine 60). This I.S. machine pulse 148 is used to establish where hot glass containers 64 from each of the sections and each of the cavities in each section are on the conveyor 62. The synchronization module 166 uses this data to identify in which of the sections and in which of the cavities in each of the sections each hot glass container 64 was molded. This information is then provided by the synchronization module 166 to the image processing module 164.

The image processing module 164 performs a variety of analyses on the images of the hot glass containers 64, which will be discussed after the operational construction of the hot glass container quality analytical system has been fully discussed herein. The image processing module 164 provides combined glass container reports and images obtained from the first infrared camera 160 to a communications module 168, which forwards this information to the server module 118. The glass container reports from the second camera module 108 and the third camera module 110 are provided to the communications module 168, which forwards them to the image processing module 164 on a data bus for combination with the glass container report generated in the image processing module 164 for images from the first infrared camera 160.

The images from the second camera module 108 and the third camera module 110 are provided to the server module 118. The image processing module 164 causes a reject pulse generator 170 to generate the reject pulse 152 used to reject any hot glass containers 64 of less than acceptable quality.

Referring next to FIG. 12, the functional details of the image processing module 164 of the first camera module 106 (shown in FIG. 11) are illustrated. The line scan input from the first camera is provided by the image acquisition module 162 to an image extraction module 180 which will extract individual images of each hot glass container 64. Referring to FIG. 13 in addition to FIG. 12, a digital "filmstrip" of images 182 is shown. The image extraction module 180 functions to obtain a frame of each hot glass container, such as the single hot glass container image frame 184 in which the single hot glass container image 186 is located, by using edge detection to determine the locations of large changes in intensity. It will be appreciated that the single hot glass container image 186, shown by itself in FIG. 14, consists of a selected number of horizontal lines and a selected number of vertical lines that are respectively determined by the vertical resolution of the first infrared camera 160 and the scan frequency.

Once the single hot glass container image 186 has been extracted by the image extraction module 180, it may be analyzed by the remaining functional modules in the image processing module 164. In a stuck ware/down ware detection module 188, the single hot glass container image 186 is analyzed to determine whether it is either a "stuck ware," where two still-plastic hot glass containers 64 come into contact with each other and become stuck together as illustrated by the stuck ware 190 illustrated in FIG. 15. Such stuck ware 190 must necessarily be rejected. The stuck ware 190 is detected by using the outline of each hot glass container image 186, which was obtained by using edge detection as mentioned above. Once the outline of the hot glass container image 186 has been determined, a stuck ware 190 may be detected by determining the width of the hot glass container image 186, typically at a location in the body of the hot glass container 64 (which is typically the widest portion of the hot glass container 64). If the width is substantially larger than it should be (even approaching double the expected width), a stuck ware determination may be made and the hot glass container 64 may be rejected.

A similar situation is that of a "down ware," where a hot glass container 64 has fallen down, as illustrated by the down ware 192 illustrated in FIG. 16. This conditions is also identified by the dimensions of the images of the hot glass container image 186. The existence of either a stuck ware 190 or a down ware 192 is communicated to a combine module 194 that is used to combine all of the glass container report information. Additionally, if no hot glass containers 64 is detected, a "missing" condition is determined and communicated to the combine module 194.

The next functional module in the image processing module 164 is a product location module 196, in which the location of the hot glass containers on the conveyor 62 in seven consecutive longitudinal locations 198, 200, 202, 204, 206, 208, and 210 on the conveyor 62. Each glass container has an ideal longitudinal location and an ideal lateral location on the conveyor 62. The ideal lateral position on the conveyor 62 is along a line extending laterally on the conveyor (it may or may not be on the centerline of the conveyor 62, depending upon the size of the glass container being manufactured), a location that is defined as Y=0, and the ideal longitudinal position on the conveyor 62 is related to the I.S. machine pulse and for each hot glass containers 64 is the desired longitudinal location on the conveyor 62 is defined as X=0.

The longitudinal offset of each hot glass containers 64 is determined by the image from the first infrared camera 160 (shown in FIG. 11) in the first camera module 106 (shown in FIG. 9) only, and the lateral offset of each hot glass containers 64 is determined by the image from both the first camera module 106 and at least one additional image, for example the image from the second camera module the second camera module 108 (also shown in FIG. 9). The longitudinal and lateral offsets are used to modify the timing of the pushers that move the hot glass containers 64 from individual section deadplates adjacent to the conveyor 62 onto the conveyor 62. The timing of the operation of the pushers controls the longitudinal offset of the hot glass containers 64 on the conveyor 62, and the angular rotation of the mechanical pusher arms controls the lateral offset of the hot glass containers 64 on the conveyor 62.

The hot glass container 64 in the longitudinal location 198 is the only one of the seven hot glass containers 64 that is in the correct location, centered both longitudinally and laterally in the longitudinal location 198 (X=0, Y=0). The hot glass container 64 in the longitudinal location 200 is ahead of where it should be (X=+2, Y=0), the hot glass container 64 in the longitudinal location 202 is behind of where it should be (X=−2, Y=0), the hot glass container 64 in the longitudinal location 204 is across the centerline from where it should be (X=0, Y=+2), the hot glass container 64 in the longitudinal location 206 is behind the centerline from where it should be (X=0, Y=−2), the hot glass container 64 in the longitudinal location 208 is ahead of where it should be and across the centerline from where it should be (X=+2, Y=+2), and the hot glass container 64 in the longitudinal location 210 is behind of where it should be and behind the centerline from where it should be (X=−2, Y=−2). The longitudinal and lateral positions of each of the hot glass containers 64 is communicated to the combine module 194.

Next, the process moves to a determine outline module 212, in which the outline of the single hot glass container image 186 (shown in FIG. 14) is determined. The outline of each hot glass container image 186 is determined by using edge detection to determine the locations of large changes in intensity. The location of such large changes in intensity define the outline of the hot glass container 64. The detected outline 214 for the single hot glass container image 186 is illustrated in FIG. 18. The outline of the hot glass container 64 is communicated to the combine module 194.

Next, the process moves to a determine middle module 216, in which the middle of each hot glass container 64 is obtained by fitting a line to the middle of the outline of the hot glass container image 186. This may be performed by finding the midpoint of the portions of each of the horizontal lines beginning and ending at the edges of the hot glass container image 186. By determining the average of these midpoints, a best fit vertical line defining the middle 218 of each hot glass container 64 may be determined. Alternately, instead of using the average of these midpoints, the median midpoint of all of the horizontal lines beginning and ending at the edges of the hot glass container image 186 may instead be used. In either case, the middle 218 of each hot glass container 64 is communicated to the combine module 194.

The process now moves to a determine lean module 220, in which edge detection is used to determine the edges of the hot glass container image 186, and to find the midpoint of each of the horizontal lines beginning and ending at the edges of the hot glass container image 186. Referring now to FIG. 20, a "leaner" 222 is illustrated. The image of the "leaner" 222 is then divided into top and bottom halves, and a best fit algorithm is used to fit a line 224 through the top half and a line through the bottom half 226 of the "leaner" 222. Next, lean is calculated for each of the top half 224 and the bottom half 226 of the "leaner" 222, and lean is calculated for the entire "leaner" 222. Using these results, it can be determined if a hot glass containers 64 is a bent neck, a base leaner, or a bent neck base leaner. The top half lean 224 and the bottom half lean 226 of each hot glass container 64 is communicated to the combine module 194.

Referring briefly to FIG. 21, alternately, a single lean only can be calculated for a "leaner" 228. Again, edge detection is used to determine the edges of the hot glass container image 186, and to find the midpoint of each of the horizontal lines beginning and ending at the edges of the hot glass container image 186. The total lean 230 is thereby calculated for the "leaner" 228, and communicated to the combine module 194.

Referring again only to FIG. 12, the process now moves to a determine horizontal distribution module 232, in which the horizontal distribution of glass in the hot glass containers 64 is determined. Horizontal distribution uses the intensity of the horizontal scan lines on each hot glass container image 186. Once again, edge detection is used to determine the edges of the hot glass container image 186, and only the portions of the horizontal lines that are between the edged of the hot glass container image 186 are used.

The center of each horizontal line on the hot glass container image 186 is determined by having equivalent sums of digital values of pixels on each side thereof. Each pixel on each horizontal scan line has a digital value, and the center of horizontal distribution is the pixel that has a roughly equivalent total digital count (the sum of the digital values of each of the pixels) on each side of the center). This may be thought of as the median location on each of the horizontal scan lines, and has nothing to do with averaging. The offset of the center from the midpoint of each horizontal line is calculated. These offsets for each horizontal line are then divided by the width of the glass container at that horizontal line (the number of pixels in that horizontal line). The horizontal distribution may then be graphically displayed for the entire height of the glass container (this will be illustrated with reference to a screenshot below). The horizontal distribution information is communicated to the combine module 194.

The process now moves to a determine vertical distribution module 234, in which the vertical distribution of glass in the hot glass containers 64 is determined. (This is what was determined as the normalized measurement-ratio curve of FIG. 4.) The determination of vertical distribution begins with a determination of the line digital value measurement for each horizontal scan line on each hot glass container image 186. For each horizontal scan line on the single hot glass container image 186, this is the sum of the digital values of each of the pixels on the horizontal scan line.

The total digital value measurement, which is the sum of the digital values of all of the pixels on all of the horizontal scan lines on the glass container, is also determined. For each horizontal scan line, the line digital value measurement is divided by the total digital value measurement to normalize the vertical distribution determination to yield a measurement-ratio value for each horizontal scan line. This removes the distance from the molds and the resultant unequal cooling between the hot glass containers 64 as factors. Thus, the measurement-ratio values for each horizontal scan line are no longer intensities but are rather dimensionless numbers. By plotting these measurement-ratio values on the X-axis against the vertical position on each of the hot glass containers 64 as the Y-axis, the vertical distribution of the glass in each of the hot glass containers 64 may be indicated. The vertical distribution information is communicated to the combine module 194.

The process then moves to a determine diameter module 236 in which information regarding the diameter of the hot glass containers 64 is obtained. Diameter information may be determined either as the diameter of a selected line or as the diameter of a selected region, either of which result in a single diameter number, or as a diameter curve for the entire glass container. The line location or the region location is programmable in the hot glass container quality analytical system of the present invention. Also, multiple line locations or region locations may be used to check diameter at a number of different heights on the glass container.

For a multiple line region (which may be, for example, 20 lines), the median diameter value in the multiple line region is preferably used, although an average could instead be used if desired. If a diameter curve is to be obtained, the diameter is calculated for each horizontal scan line on the single hot glass container image 186, and such a diameter curve may be displayed as a curve (by plotting the calculated diameter values for each horizontal scan line on the X-axis against the vertical position on each of the hot glass containers 64 as the Y-axis). The diameter information is also communicated to the combine module 194.

Referring next to FIG. 22, the flow of formatted data used to generate a combined report is illustrated. The image from a first camera image 240 is provided to an image extraction module 242, which extracts images of the hot glass containers 64. The images are provided to a stuck ware/down ware module 244 which will identify stuck ware and/or down ware based on width characteristics (and, in the case of down ware, height characteristics) of the image. The images are also provided to a product location module 246, which identifies the location of the hot glass containers 64 on the conveyor 62 (shown in FIG. 8). It will be appreciated that the product location module 246 must also have images obtained from another camera in order to provide both longitudinal and lateral displacement information regarding the hot glass containers 64 on the conveyor 62. Formatted image data regarding product location is supplied from the product location module 246 to a formatted image data bus 248.

The image information from the product location module 246 is also provided to an outline detection module 250, which uses edge detection to identify the outline of the glass containers. This data is provided to a center line determination module 252 that determines the best fit center line of the outline of the glass containers and provides formatted image data of the same to the formatted image data bus 248. A lean determination module 254 determines the lean of the outline of the glass containers and provides formatted image data of the same to the formatted image data bus 248.

A horizontal distribution determination module 256 determines the horizontal distribution of the outline of the glass containers and provides formatted image data of the same to the formatted image data bus 248. A vertical distribution determination module 258 determines the vertical distribution of the outline of the glass containers and provides formatted image data of the same to the formatted image data bus 248. A diameter determination module 260 determines the diameter of the outline of the glass containers and provides formatted image data of the same to the formatted image data bus 248. The formatted image data from the formatted image data bus 248 is used together with formatted image data from reports from other camera modules 262 to generate combined report data 264.

Figure 23:
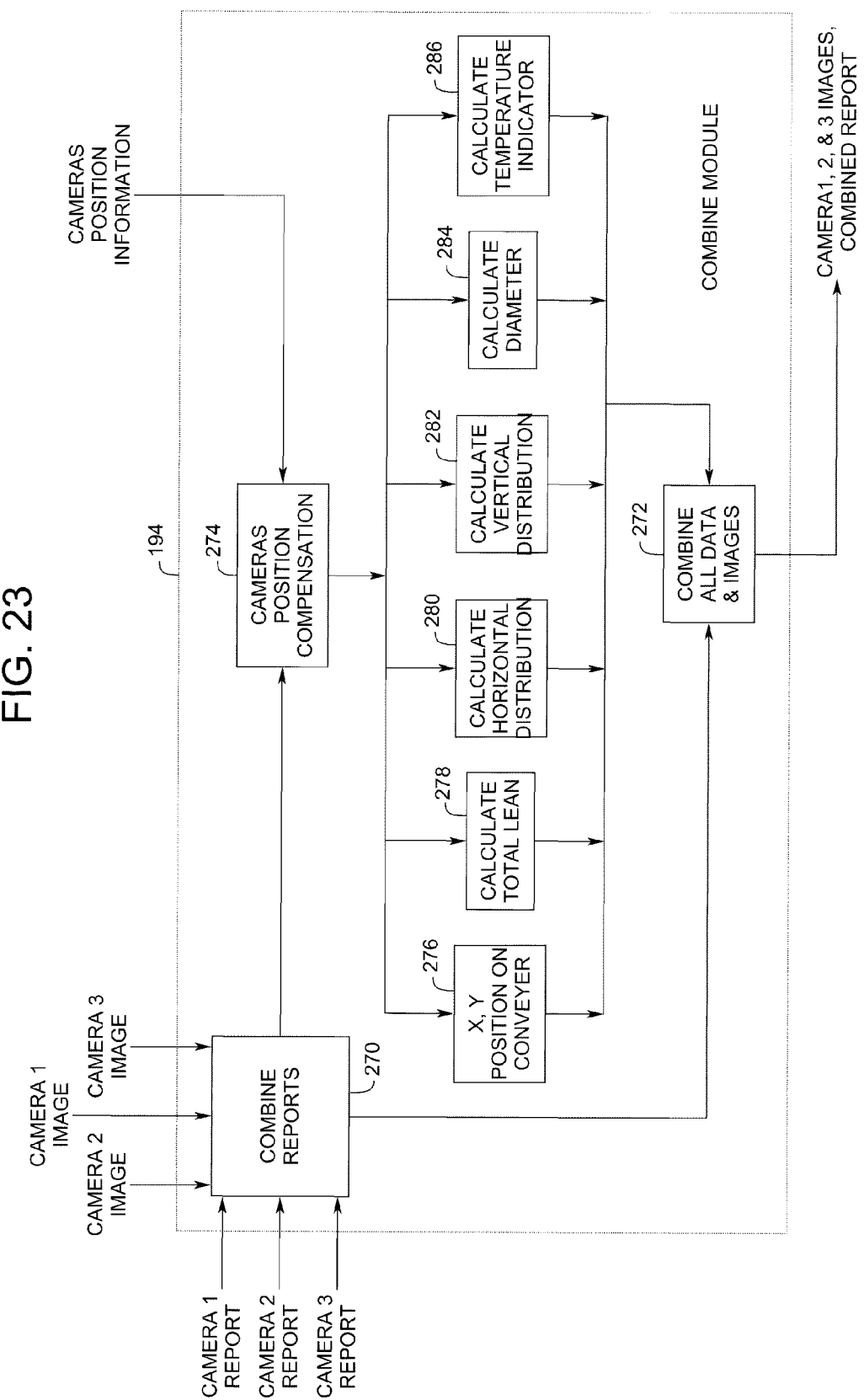
FIG. 23 is a schematic depiction showing the combination of data occurring in the combine module illustrated in FIG. 12.

Referring now to FIG. 23, the combination of report data and images from a plurality of camera modules as inputs to the combine module 194 (FIG. 12) to produce the combined report and the images as outputs is illustrated. It will be understood that the images essentially flow through the combine module 194, although they may be annotated for display on user interface modules (not illustrated herein). The images from three cameras and the report data from three camera modules are provided as inputs to a combine reports module 270, which provides the images to a combine data and images module 272.

The report data is provided to a camera position compensation module 274, which also has as an input information defining the relative positions of the cameras. The camera position compensation module 274 provides its output to six modules that perform final calculations based upon the information contained in the three camera reports. An X, Y position calculation module 276 uses the information obtained from multiple reports to determine the longitudinal and lateral displacement of each hot glass container 64 on the conveyor 62, and provides this information to the combine data and images module 272. A total lean calculation module 278 uses the information obtained from multiple reports to determine the total lean of each hot glass container 64, and provides this information to the combine data and images module 272.

A horizontal distribution determination module 280 uses the information obtained from multiple reports to determine the horizontal distribution of each hot glass container 64, and provides this information to the combine data and images module 272. A vertical distribution calculation module 282 uses the information obtained from multiple reports to determine the vertical distribution of each hot glass container 64, and provides this information to the combine data and images module 272. A diameter calculation module 284 uses the information obtained from multiple reports to determine the diameter of each hot glass container 64, and provides this information to the combine data and images module 272. A temperature calculation module 286 uses the information obtained from multiple reports to determine the temperature of each hot glass container 64, and provides this information to the combine data and images module 272.

The manners in which the calculations identified in FIG. 23 are made is described with reference to FIG. 24. First camera image and data 290, second camera image and data 292, and third camera image and data 294 are combined to produce combined report data 296 which is interfaced with camera position angle and time data 298 to produce combined object data that is provided to a combined object data bus 300. However, in the following discussion of FIG. 24, is will be assumed that two cameras are used, and the third (shown in dotted lines) is optional and not used for the purposes of this discussion. An X, Y position determination module 302 uses determines the longitudinal and lateral displacement of each hot glass container 64 on the conveyor 62, and produces combined object data that is provided to a combined object data bus 300.

A total lean determination module 304 uses the lean calculations made for the hot glass container image for each of the images from the two cameras. Both the lean and the sign of the lean (positive or negative) is determined for each of the images from the cameras, and the leans and their signs are then used to calculate total lean taking into account the relative angular positions of the cameras. If the total lean for a glass container calculated in this manner is excessive, the glass container will be rejected for lean. The total lean determination module 304 produces combined object data that is provided to the combined object data bus 300.

A horizontal distribution determination module 306 uses the horizontal distribution calculations made for the hot glass container image for each of the images from the two cameras. It will be recalled that the offset of the center of intensity from the midpoint of each horizontal line in each hot glass container image was calculated, and then divided by the width of that hot glass container image at that horizontal line. In combining the horizontal distribution data from two camera images, the larger value for each horizontal line from the two camera images is used to determine the offset for that horizontal line. The horizontal distribution determination module 306 produces combined object data that is provided to the combined object data bus 300.

A vertical distribution determination module 308 preferably uses the vertical distribution calculations made for the hot glass container image from only one of the images from the two cameras (preferably from the first camera, which is located orthogonally with respect to the conveyor 62 (FIG. 8). Due to the nature of vertical distribution, it is not believed to be necessary to use the vertical distribution calculations made for the hot glass container images from both of the two cameras, although the calculations for each horizontal line could instead be averaged. The vertical distribution determination module 308 produces combined object data that is provided to the combined object data bus 300.

A diameter determination module 310 preferably uses the diameter calculations made for the hot glass container image from only one of the images from the two cameras (preferably from the first camera, which is located orthogonally with respect to the conveyor 62 (FIG. 8). Due to the nature of the diameter, it is not believed to be necessary to use the diameter calculations made for the hot glass container images from both of the two cameras, although the calculations for diameters from the two cameras could instead be compared and/or averaged on a horizontal scan line by horizontal scan line basis. In a preferred embodiment, if the two diameters differ an indication is provided that the glass container is not round, and if the difference is too large the glass container would be rejected. The diameter determination module 310 produces combined object data that is provided to the combined object data bus 300.

A temperature determination module 312 is used to provide an indication of temperature by determining the sum of the digital values of all of the pixels on all of the horizontal scan lines on the image of each glass container. Due to the nature of the temperature, it is not believed to be necessary to use the temperature calculations made for the hot glass container images from both of the two cameras, although the calculations could instead be averaged. In addition, a plot of the median values by mold may also be made, for example from the coolest mold (the furthest away) to the hottest mold (the closest), with a best fit line being plotted from the median values. The temperature determination module 312 produces combined object data that is provided to the combined object data bus 300.

In monitoring the hot glass containers as they stream from the I.S. machine where they are molded, the philosophy of the hot glass container quality analytical system of the present invention differs from that of merely checking each glass container against some arbitrary "perfect" glass container standard. Instead, the initial assumption is made that at least eighty percent of the glass containers being manufactured are of acceptable quality, and that less than twenty percent of the glass containers being manufactured are of lesser quality. The objective of the hot glass container quality analytical system of the present invention is to correct that twenty percent. Thus, the overriding objective of the hot glass container quality analytical system is not to make glass containers "perfect" according to some predefined standard, but rather to make them consistently so that they are all essentially the same. In order to do so, the aim is to present information to the operator of the I.S. machine that identifies outliers, and thereby assists the operator to adjust the I.S. machine to bring the outliers more into conformity with the others.

In this regard, many of the characteristics of each hot glass container that are determined by the hot glass container quality analytical system of the present invention are compared with a baseline value that is determined according in a novel manner. The values of each determined characteristic for each hot glass container that are determined by the hot glass container quality analytical system are stored on a first in, first out manner for a predetermined time period that may be varied. In a preferred embodiment, that characteristic is thirty minutes, although it could be varied from as little as one minute to as much as twenty-five hours, or even longer.

An example of the use of the median from the last thirty minutes (the predetermined period) is the calculation of the diameter at a particular location on the hot glass containers. When the diameter value at a particular location on a hot glass container or the diameter curve for a hot glass container has been determined, it can be compared with a value or a curve that is the median value (or a curve that contains the median values of each horizontal scan line) determined over the last thirty minutes, which may be shown as a solid line or a solid curve on the display.

From the values for each determined characteristic for each hot glass container for the predetermined period, the median values for each characteristic at that point in time are selected, and the determined characteristics for the current hot glass container may be compared with these median characteristics. It will be appreciated that the determination of the median characteristics occurs with every hot class container, since the predetermined period (e.g., thirty minutes) will change for each consecutive glass container. The median characteristics may be visually displayed (typically as a solid line) together with the image of the hot glass container. This is an important distinction from the operation of European Patent Application No. EP 09075545.5, filed on Dec. 10, 2009, and assigned to the assignee of the present patent application.

An important advantage of the hot glass container quality analytical system of the present invention is that since it normalizes the image information for the hot glass containers, it can render unnecessary the determination of different medians for some of the characteristics of hot glass containers coming from different sections or molds that are based upon temperature variations of the hot glass containers coming from these different sections and molds. For example, consider the determination of vertical distribution of glass in the hot glass containers. Since information derived from the image for each hot glass container for vertical distribution is normalized by dividing the line radiation measurement for each image line by the total radiation measurement, differences occurring due to unequal cooling of the hot glass containers was eliminated.

Thus, each determined characteristic for each hot glass container may be compared with its median value for the predetermined period (e.g., thirty minutes), and information may be provided that may accompany the visual display of the image of that hot glass container. Additionally, determinations of warnings or rejections of that hot glass container may be made based upon how much the determined characteristics vary from the median values for those determined characteristics. For example, a percentage deviation (positive or negative) from the median value for each determined characteristic may be set, so that any hot glass container that exceeds this percentage deviation for any determined characteristic will be rejected. Further, two lower percentage deviations (such as, for example, one-third and two-thirds of the percentage deviation required for rejection) may be cause for a warning to be presented or an alarm to be raised for the determined characteristic for the hot glass container. Alternately, the levels for each of warnings, alarms, and rejects may be individually selectable. Information regarding rejections, alarms, or warnings may also be visually displayed for each glass container, as will become apparent below in conjunction with the discussion of the screenshots.

An example of a manner in which determined characteristics may be displayed for a particular mold may be provided for determined temperature, the process for which determines the sum of the digital values of all of the pixels on all of the horizontal scan lines on a hot glass container. The median temperature indicator for all of the hot glass containers coming from each mold for the last half hour may be used as a comparison value. Thus, the temperature indicator for each hot glass container is compared to the median temperature indicator for the hot glass containers coming from the same mold for the last half hour (the predetermined period), with a percentage difference being indicated. In addition, a plot of the median values by mold may also be made, for example from the coolest mold (the furthest away) to the hottest mold (the closest), with a best fit line being plotted from the median values. Preferably, for the temperature determination, only one camera is used, preferably the first camera that is mounted orthogonally with respect to the conveyor.

Figure 25:
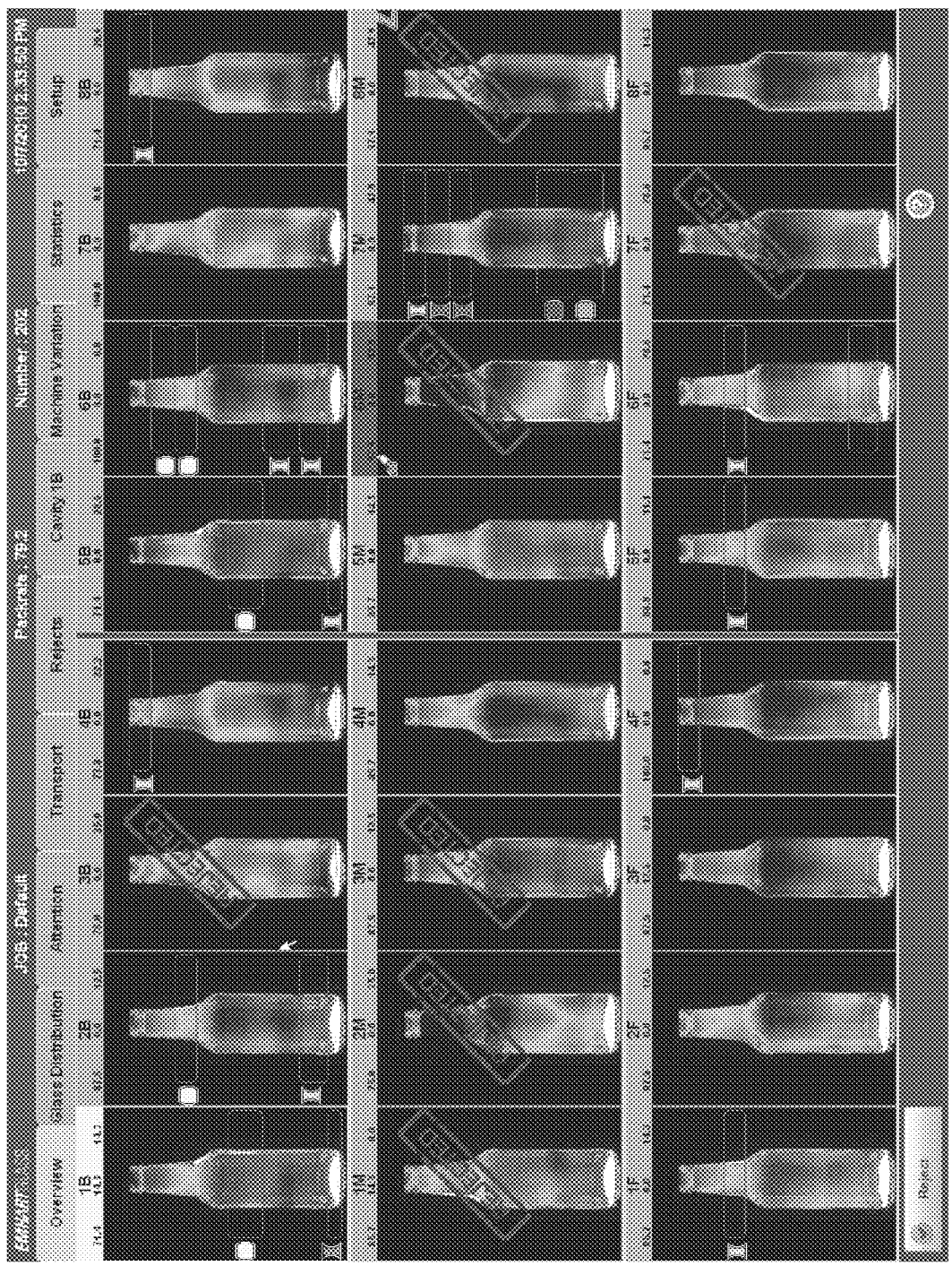
FIG. 25 is a screenshot of the display of a touchscreen user interface module showing an Overview screen in which the last glass container imaged from each mold in each section of the I.S. machine is simultaneously displayed and updated in real time.

A number of screenshots that would be displayed on a touchscreen user interface module are also provided. Referring first to FIG. 25, an Overview screen is shown for an eight section, three mold I.S. machine. The screen is arranged to show a hot glass container from each of the molds in each of the sections, and is a real-time display of hot glass containers as they are monitored and analyzed by the hot glass container quality analytical system of the present invention. An image of each of the hot glass containers is both displayed and updated in real time.

In the preferred embodiment, the images are displayed in color using a color code keyed to the digital value representative of the radiation at each pixel of the images. For example, the hottest regions can be displayed as red, moving to orange, yellow, green, blue, and dark blue as the digital value of a pixel drops. The background of the containers, where the digital values are the lowest since the background is relatively cool compared to the hot glass bottle, may be arbitrarily displayed as black, as shown in FIG. 25, or, alternately, as white for purposes of contrast with the hot glass containers.

It may be seen that a number of the images of hot glass containers have been prominently labeled as rejected, and warnings are displayed on a number of other images of hot glass containers. At the top of the screen it may be seen that there are a number of tabs that may be used to access various screens contained in the hot glass container quality analytical system of the present invention. Since the user interface module is preferably touchscreen, a user can touch any of these tabs to access the other screens. By touching the ? icon in the lower right of the screen, a help screen for the currently displayed screen may be accessed. By touching the Reject button in the lower left corner, the hot glass container quality analytical system can be enabled to reject hot glass containers that meet the reject criteria, or to allow all of the hot glass containers to pass through on the conveyor.

Figure 26:
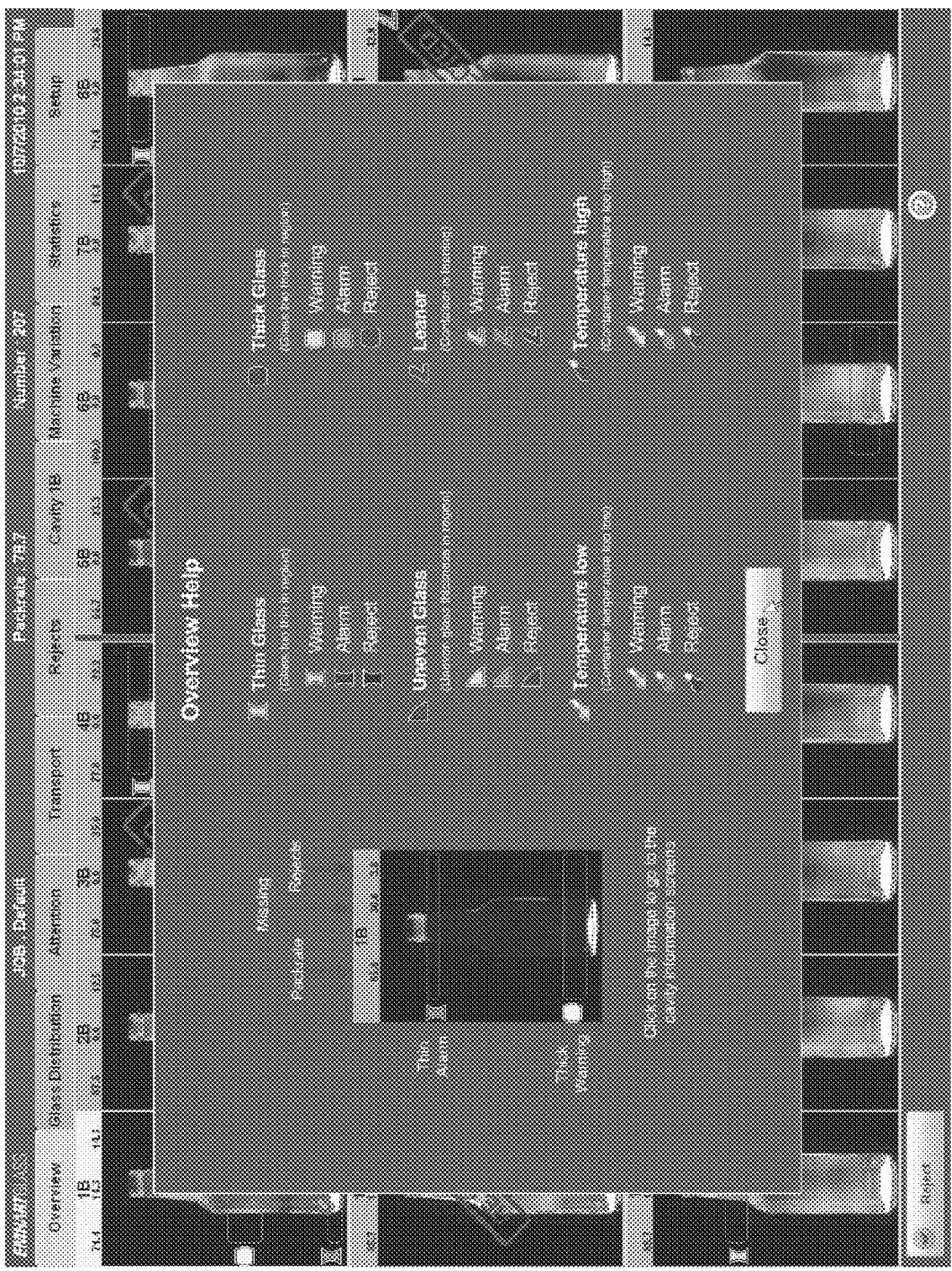
FIG. 26 is a screenshot of the Help screen for the Overview screen of FIG. 25, showing an index for many of the symbols used in the Overview screen.

Referring next to FIG. 26 in conjunction with FIG. 25, the Overview Help screen is shown as being superimposed upon the Overview screen of FIG. 25. The Overview Help screen provides a legend for the various icons that may be used in the Overview screen. Unique icons are provided for thin glass, thick glass, uneven glass, leaners, and high or low temperatures. Three icons are provided for each of these categories of problems, with the icons preferably being colored yellow for warnings, orange for alarms, and red for rejections. Also the location of information on packrate, missing glass containers, and rejects for each mold is highlighted.

Figure 27A:
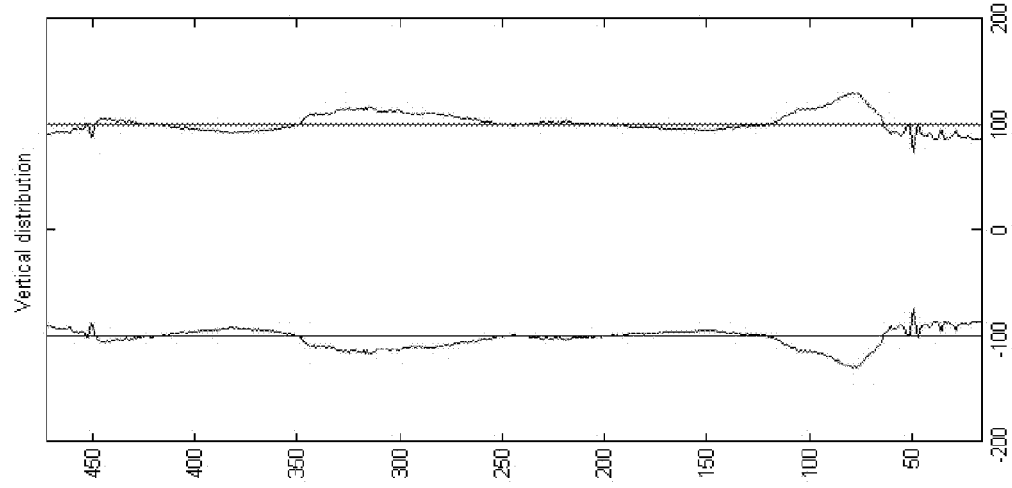
FIGS. 27A-C are displays of a Vertical Distribution, a Horizontal Distribution, and a Glass Distribution with both Vertical Distribution and Horizontal Distribution, respectively.

One of the innovations of the hot glass container quality analytical system of the present invention is that vertical glass distribution and horizontal glass distribution may be shown for a hot glass container in unified fashion. In the past, vertical glass distribution has been presented as a curve. (The present invention is also capable of presenting horizontal glass distribution as a curve. Referring now to FIG. 27A, the vertical glass distribution is presented as a solid plot rather than as a curve.) The solid plot is shown with respect to a rectangle which is the height of the vertical glass distribution curve and which has a volume representative of the amount of glass that should be contained in each of the hot glass containers.

The vertical glass distribution curve is placed over the right side of the rectangle with its average point(s) overlying the right side of the rectangle, and with its mirror image placed over the left side of the rectangle with the mirror image's average point(s) overlying the left side of the rectangle. The volume contained within the vertical glass distribution plot lying between these vertical glass distribution curves should be the same as the volume of the rectangle (assuming that the hot glass container contains the proper volume of glass). Thus, by looking at the visual depiction displayed in the vertical glass distribution plot, one can quickly understand the vertical glass distribution in the hot glass container.

Figure 27B:
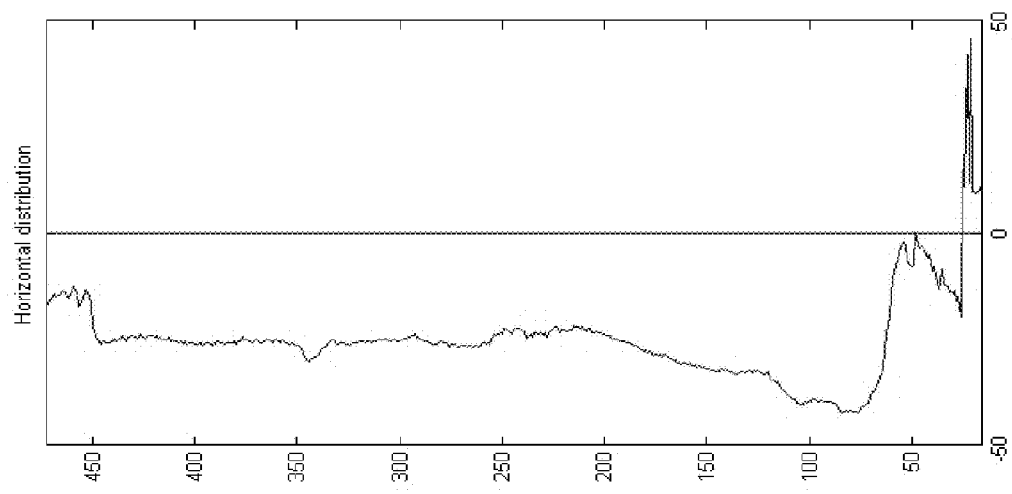

Referring next to FIG. 27B, a horizontal glass distribution curve is illustrated for the same hot glass container. The horizontal glass distribution curve, of course, is plotted along a vertical line indicating the middle of the hot glass container, and ideally would coincide with that vertical line. To the extent that it does not, the horizontal glass distribution curve thus illustrates an unequal horizontal distribution of glass in the hot glass container at the locations at which it diverges from the vertical line. The horizontal glass distribution curve illustrated in FIG. 27B shows an improper distribution to the left.

Figure 27C:
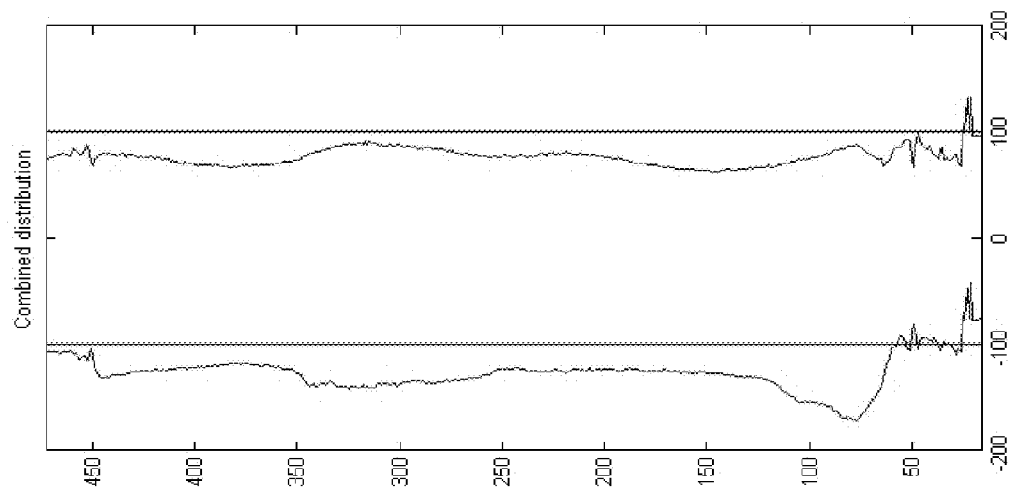

Referring now to FIG. 27C, the horizontal distribution curve has been added to each of the vertical glass distribution curve and its mirror image, thereby resulting in a glass distribution plot that combines the vertical glass distribution curve and the horizontal distribution curve together into a single plot. A user looking at the glass distribution plot of FIG. 27C can clearly understand both the vertical glass and the horizontal distribution of glass in the hot glass container.

This represents a significant advancement in the presentation of glass distribution information.

Figure 28:
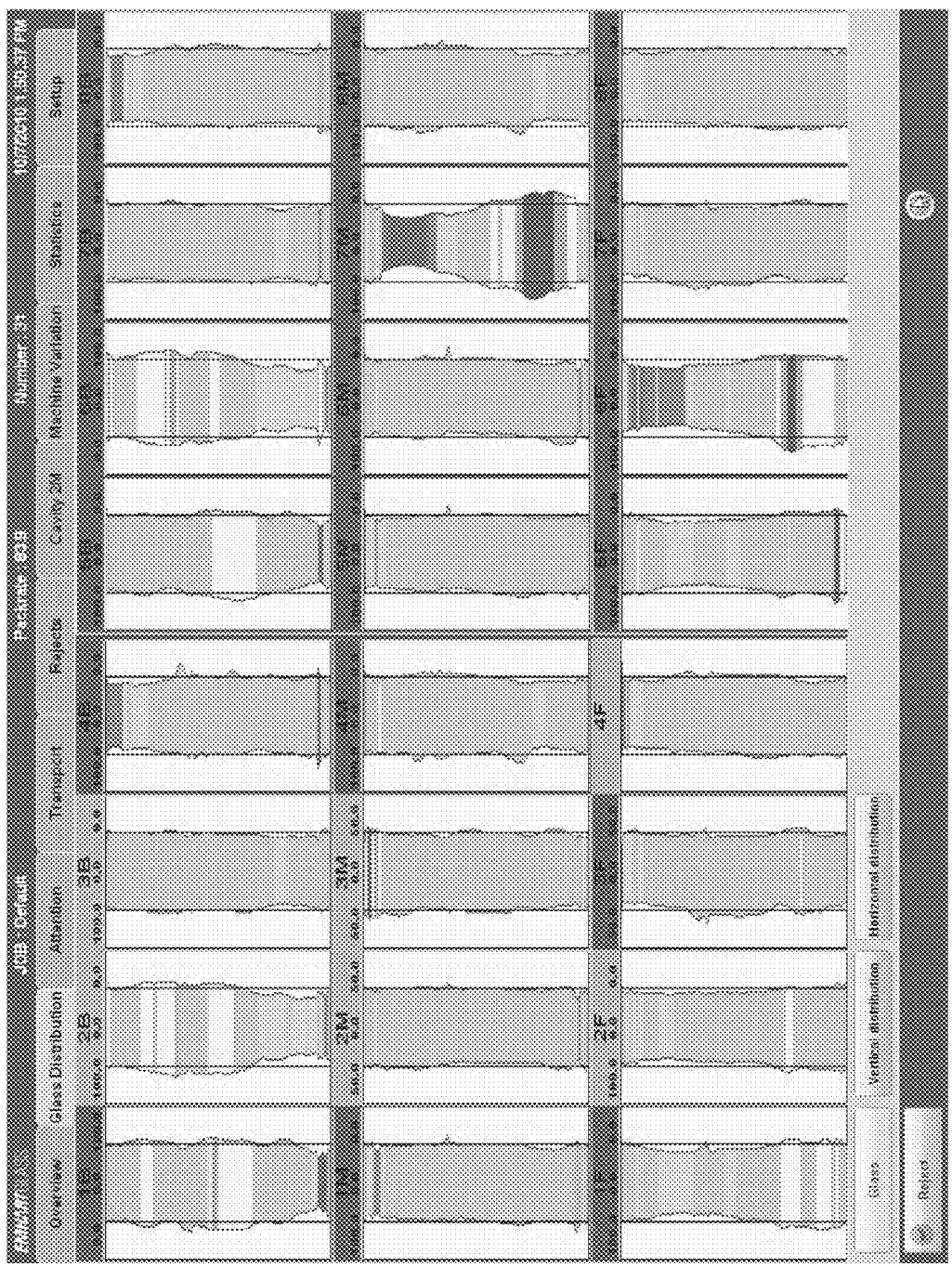
FIG. 28 is a screenshot of the Glass Distribution screen which shows both Vertical Distribution and Horizontal Distribution.

Referring now to FIG. 28, a Glass Distribution screen is shown for an eight section, three mold I.S. machine. It will be appreciated that the areas of each glass distribution plot that are wither to thick, too thin, or in which the horizontal distribution is improper will be illustrated by horizontal bands of color. The bands of color may be different for warnings, alarms, and rejections, if desired (and as shown in FIG. 28). Like the Overview screen illustrated in FIG. 25, image of each of the glass distribution curves for each of the hot glass containers from each of the molds in each of the sections is both displayed and updated in real time.

Figure 29:
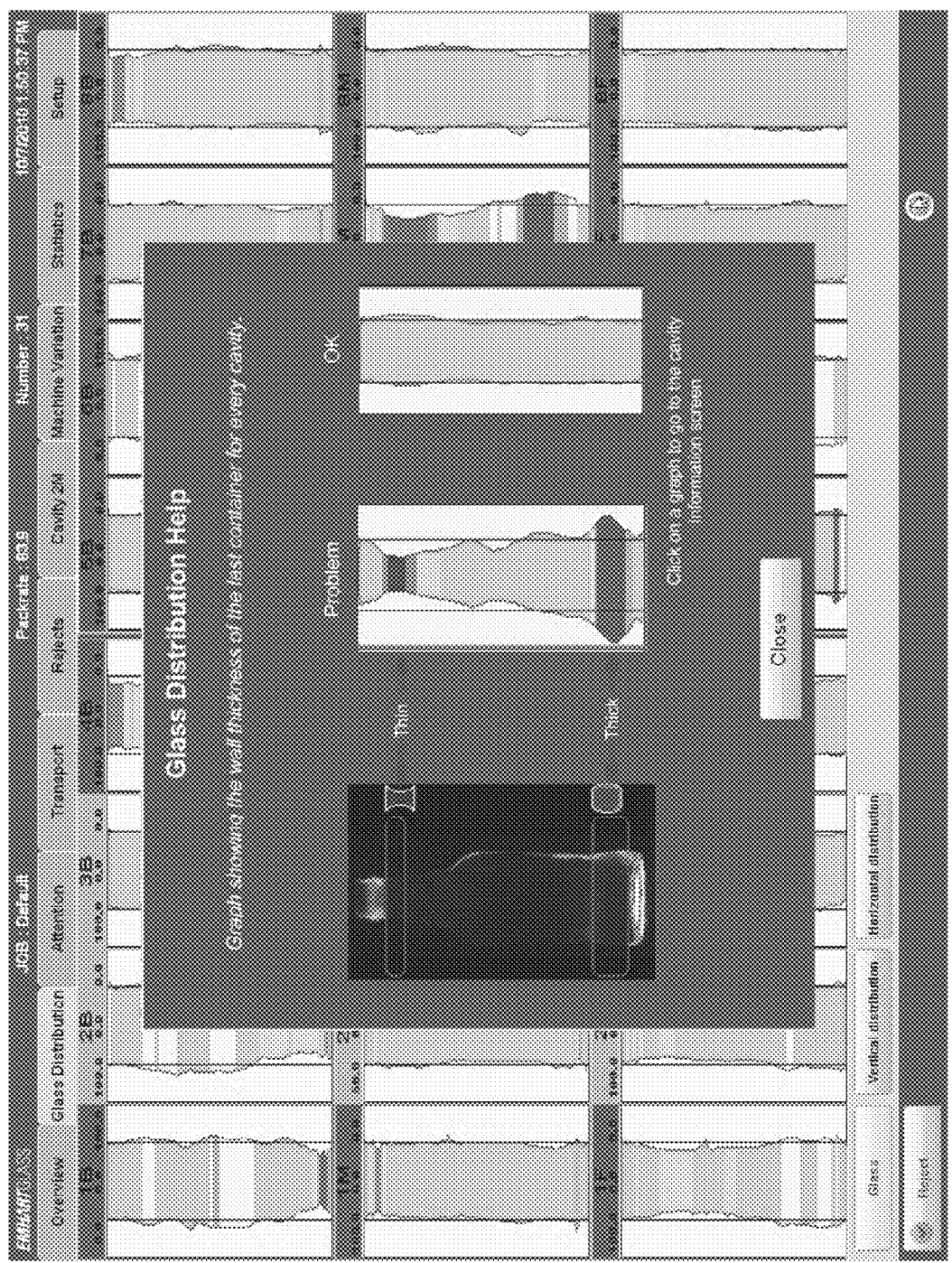
FIG. 29 is a screenshot of the Help screen for the Glass Distribution screen of FIG. 28, providing explanations for the information that is displayed in the Glass Distribution screen.

FIG. 29 is Glass Distribution Help screen that is shown as being superimposed upon the Glass Distribution screen of FIG. 28. The Glass Distribution Help screen provides a legend for the thick and thin icons that are used in the Glass Distribution screen. A problem glass distribution display as well as an acceptable glass distribution display are also shown in the Glass Distribution Help screen.

Figure 30:
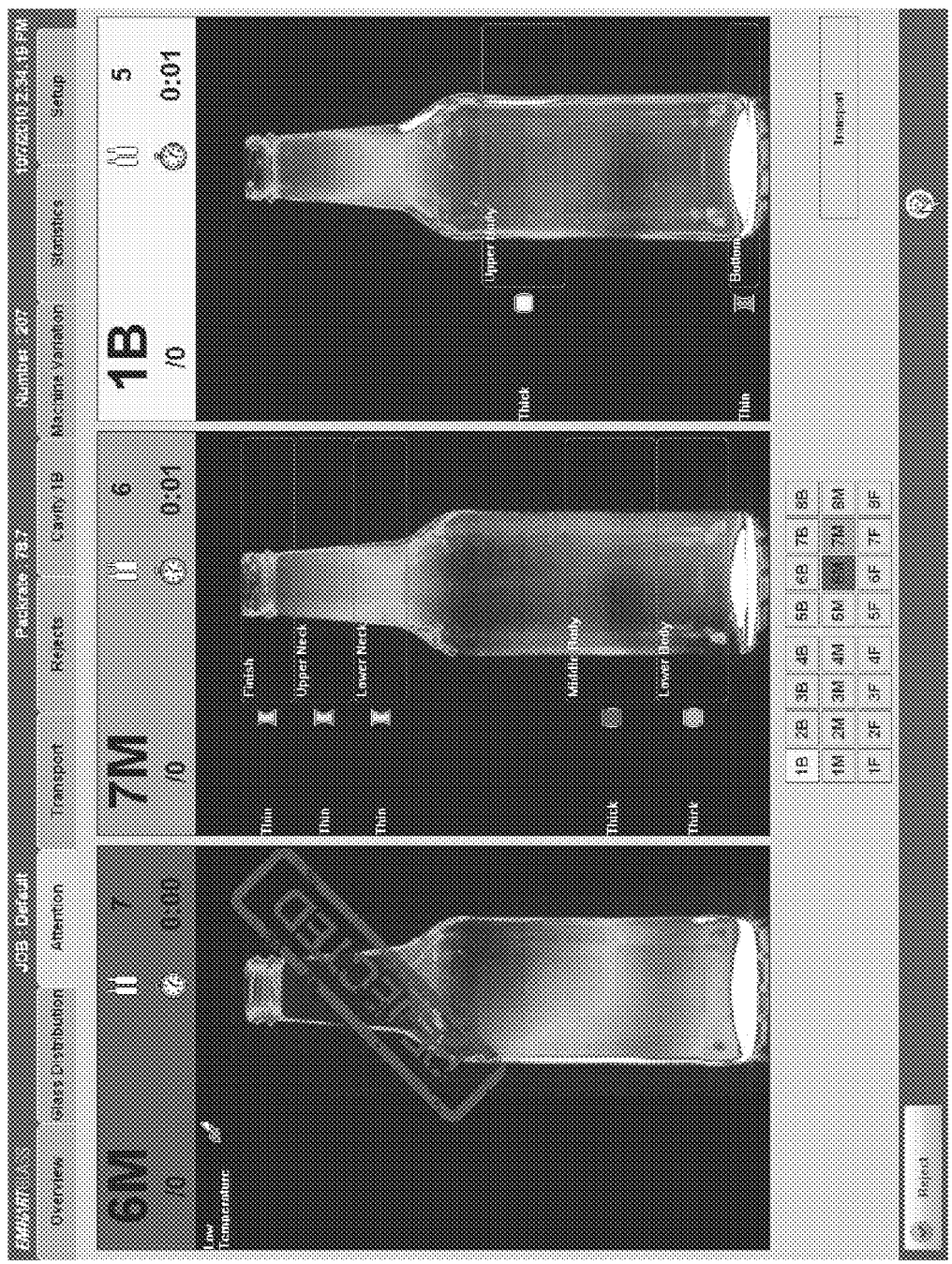
FIG. 30 is a screenshot of the Attention screen which shows the three worst producing molds of the I.S. machine.

Referring next to FIG. 30, an Attention screen is shown which shows the three worst producing molds of the I.S. machine (over the last predetermined period, e.g., thirty minutes). In the preferred embodiment, the relative quality of the worst three are identified by the color of the band at the top of each of the three images of the hot glass containers, with red being the worst glass container, orange being the second worst glass container, and yellow being the third worst glass container. The location of each of the three worst hot glass containers is also shown in a schematic illustration showing the sections and molds.

Figure 31:
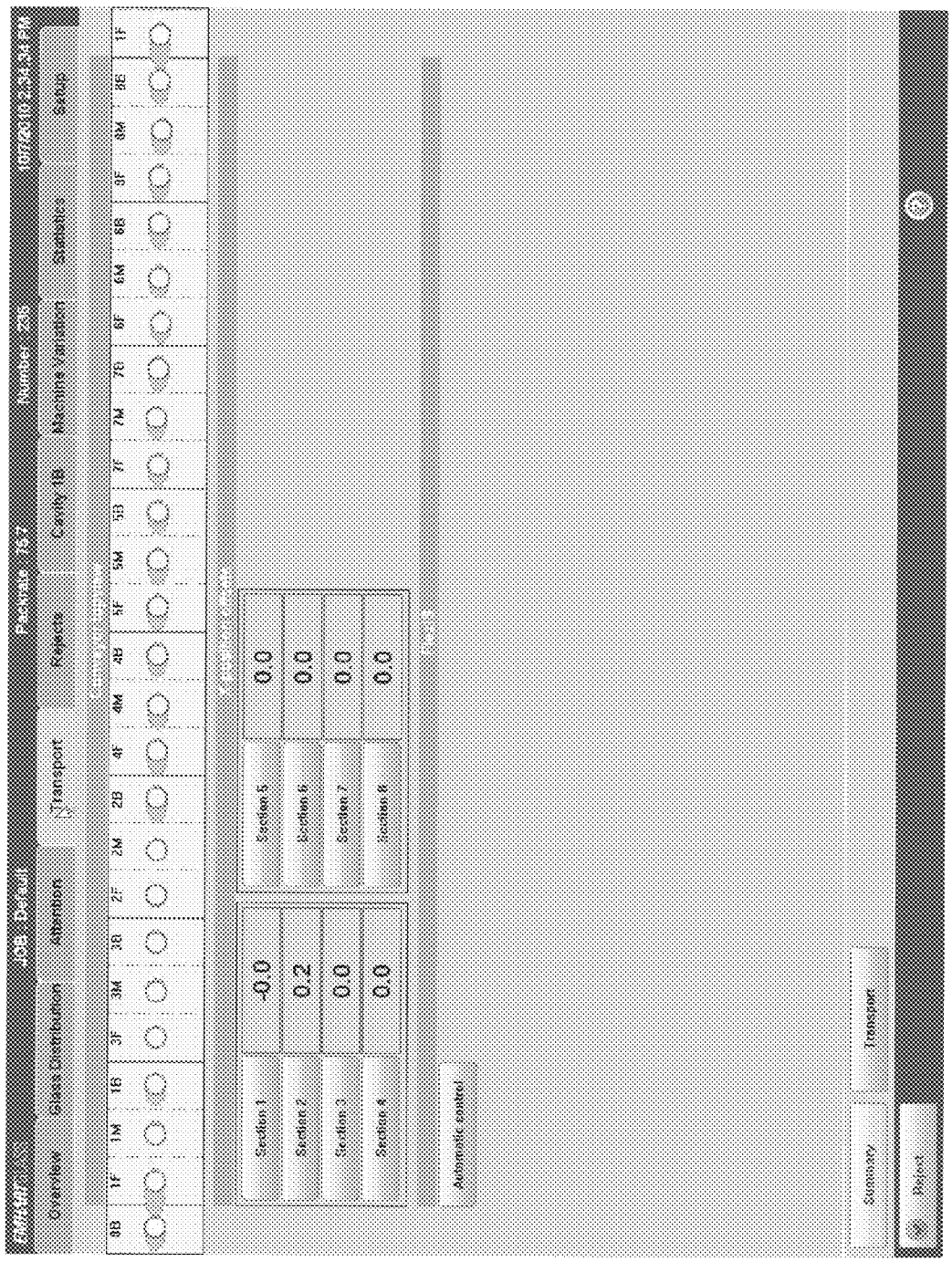
FIG. 31 is a screenshot of the Transport screen showing the real time location of hot glass containers on the conveyor for each mold as well as the variation in positions over a selected time period.
Figure 32:
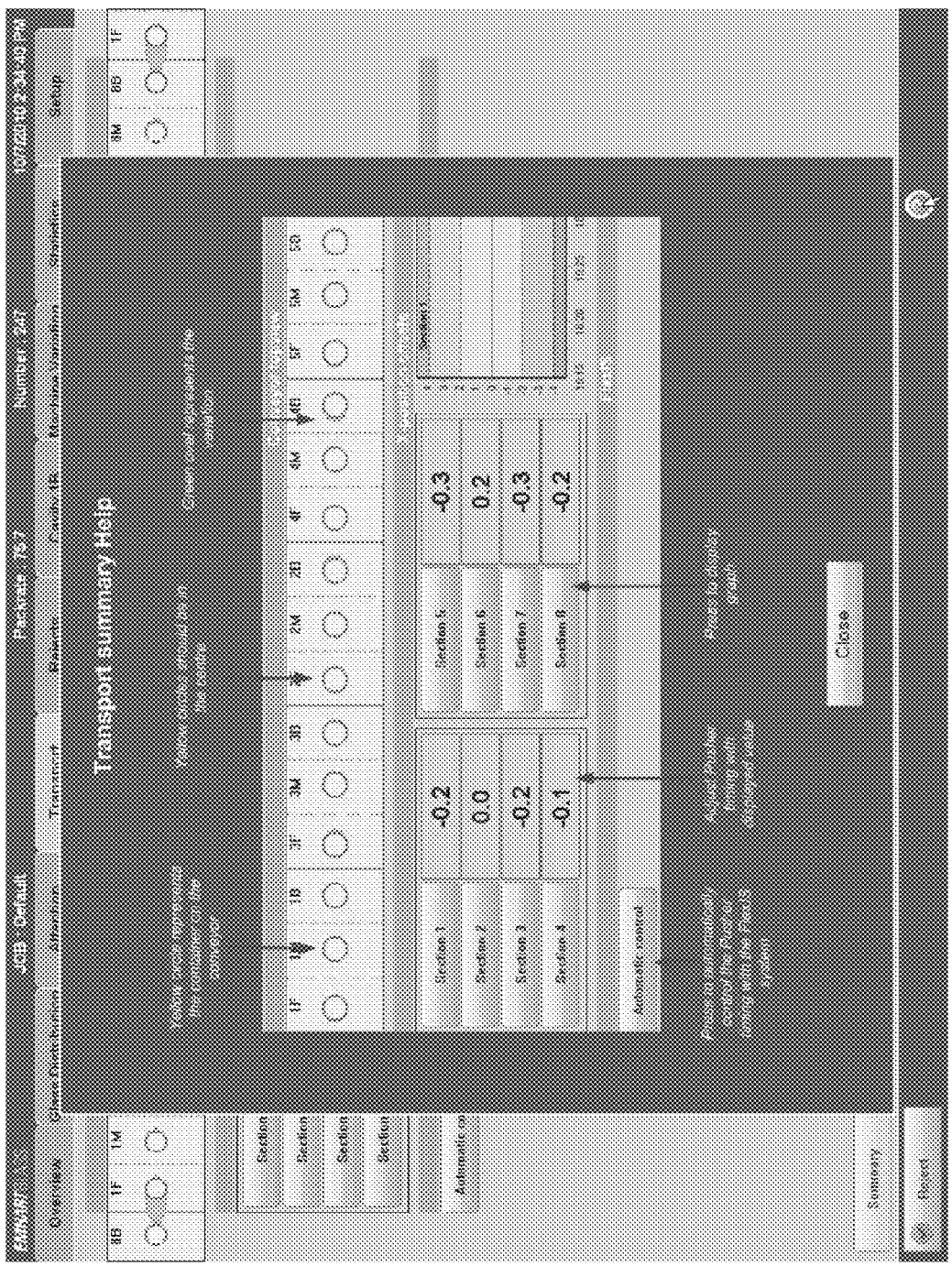
FIG. 32 is a screenshot of the Help screen for the Transport screen of FIG. 31, providing explanations for the information that is displayed in the Transport screen.

Referring now to FIG. 31, a Transport screen is shown that depicts the real time location of the last hot glass containers from each section and mold on the conveyor as well as the variation in positions over a selected time period. FIG. 32 is Transport Help screen that is shown as being superimposed upon the Transport screen of FIG. 31. The location of each hot glass container is shown by the circle, with variations in the locations of hot glass containers for the last predetermined time (e.g., thirty minutes) being shown by the shaded areas around the circles. Adjustments to the movement of the pusher mechanisms (the pusher mechanism pushes glass containers formed in the I.S. machine from a dead plate to the conveyor) may also be made, which will control to some degree the positions of the hot glass containers on the conveyor. The positions of a hot glass container from each mold in each section is both displayed and updated in real time in the Transport screen.

Figure 33:
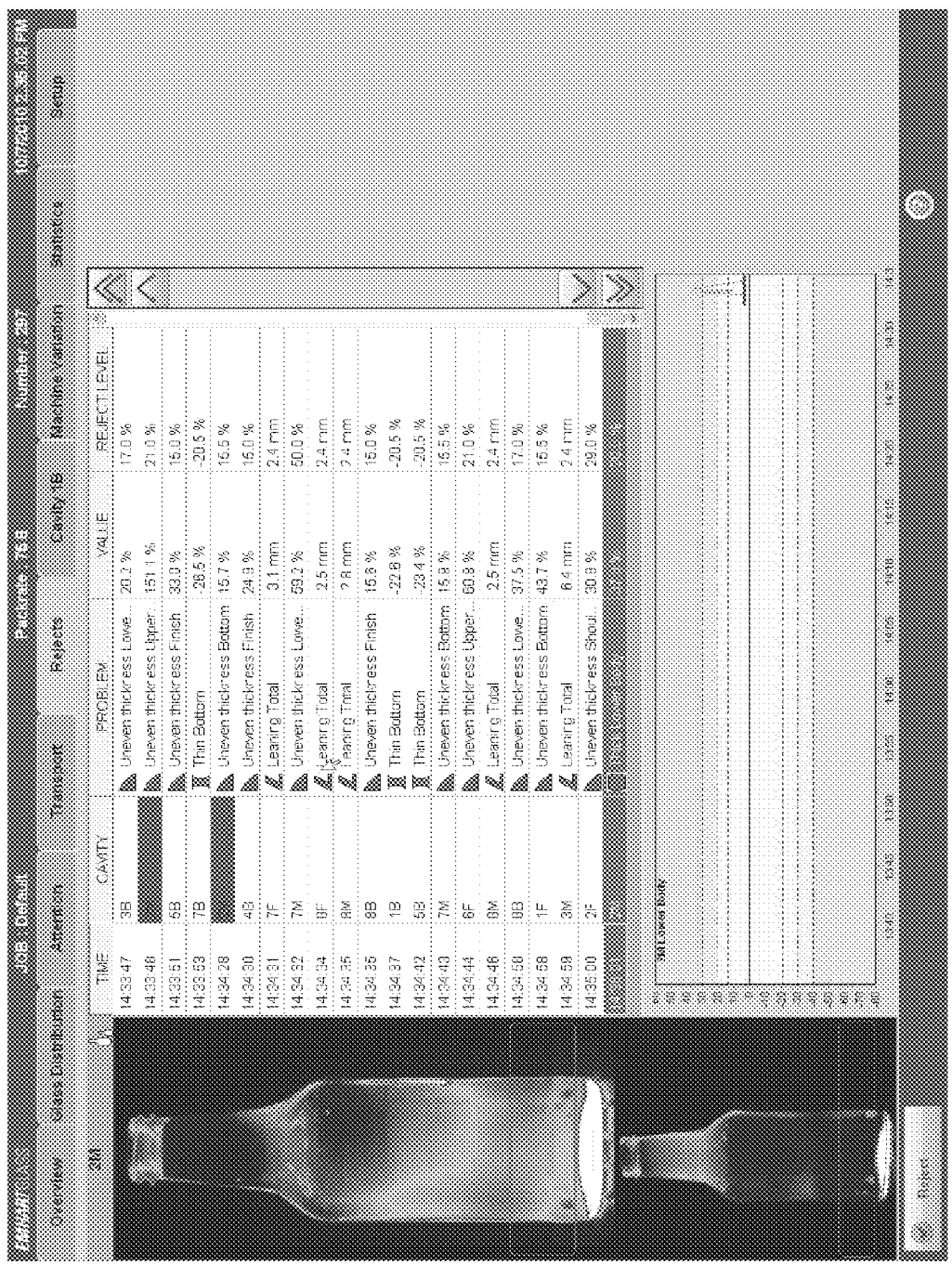
FIG. 33 is a screenshot of the Rejects screen showing summary information about the glass containers that have been rejected including the basis for their rejection.

Referring next to FIG. 33, a Reject screen is shown which shows data regarding hot glass containers that have been rejected, including the particular problem resulting in the rejection. The data is shown as being arranged by time of rejection.

Figure 34:
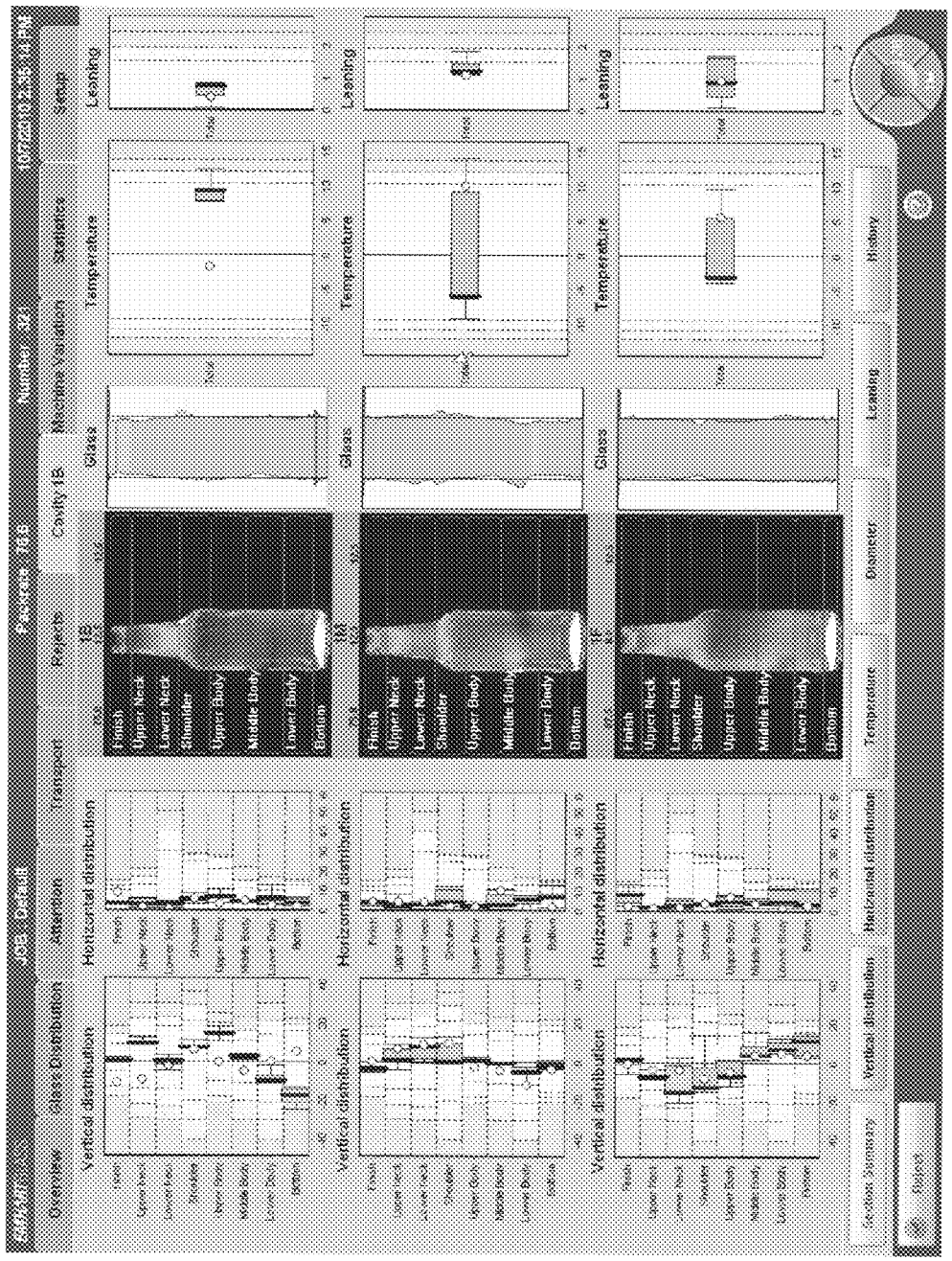
FIG. 34 is a screenshot of the a Section Summary screen for one of the sections of the I.S. machine, displaying a large amount of information regarding glass containers produced by that section.
Figure 35:
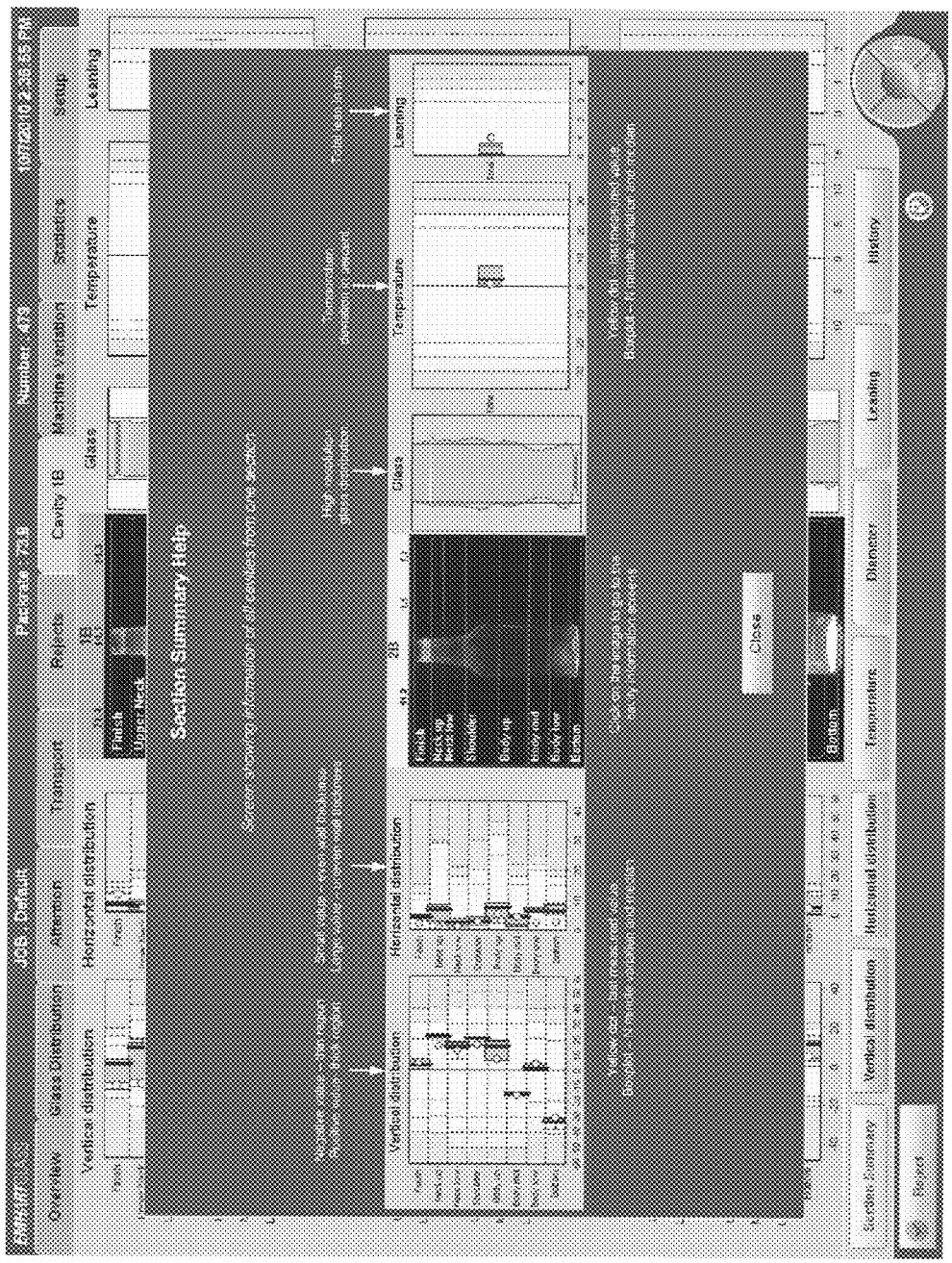
FIG. 35 is a screenshot of the Help for the Section Summary screen of FIG. 34, providing explanations for the information that is displayed in the Section Summary screen.
Figure 36:
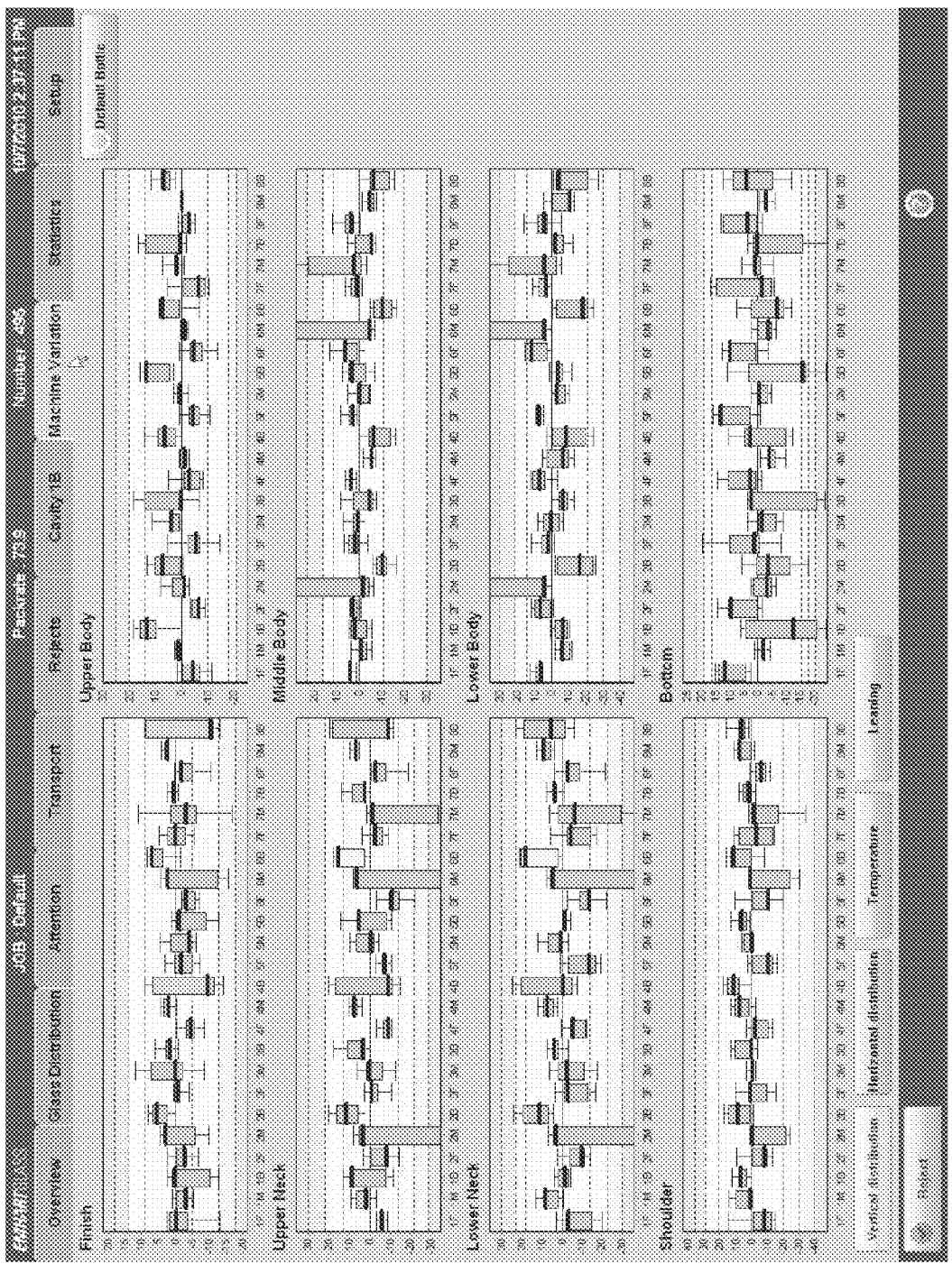
FIG. 36 is a screenshot of the Machine Variation Vertical Distribution screen showing summary information about the vertical distribution of glass in the glass containers produced by the I.S. machine.
Figure 37:
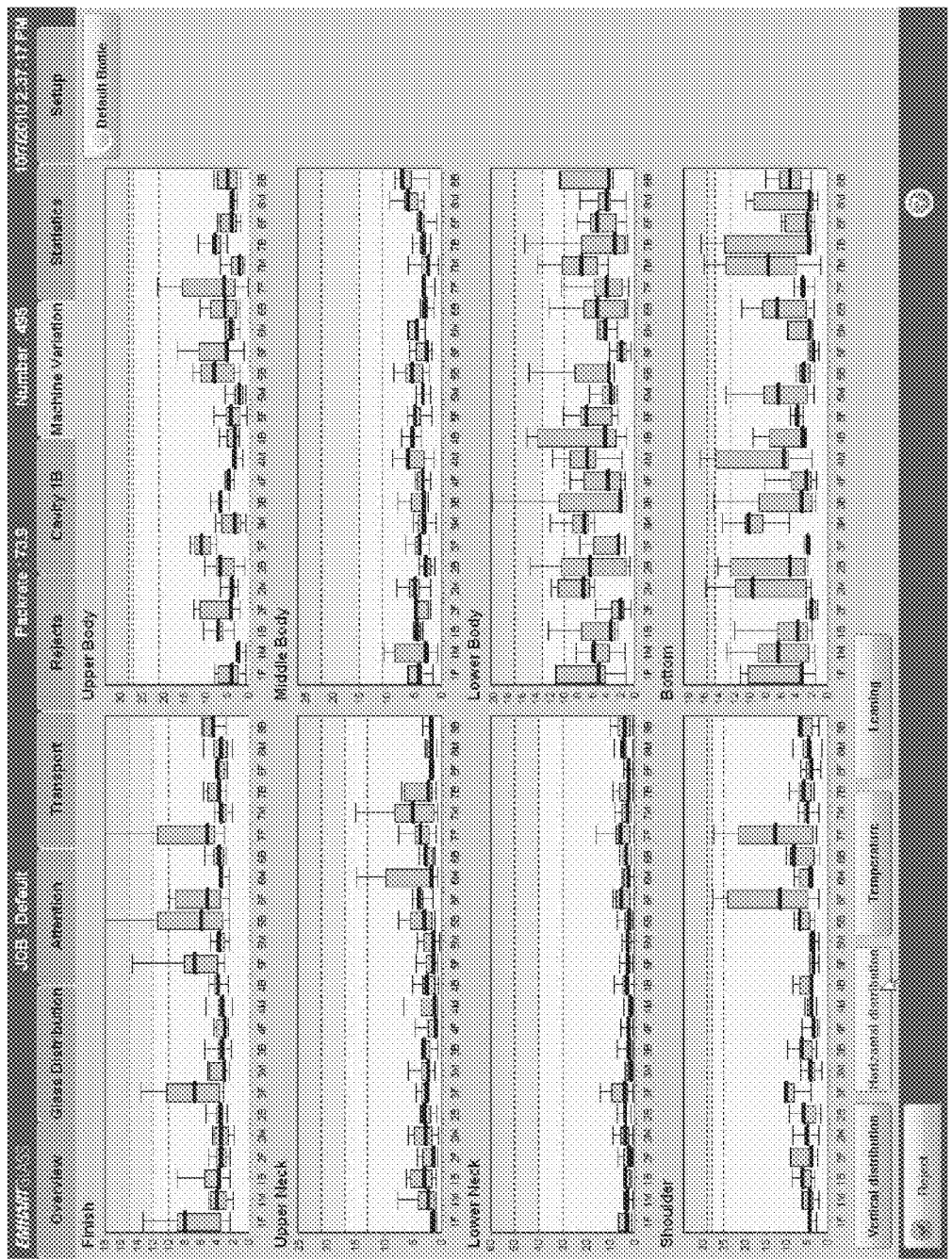
FIG. 37 is a screenshot of the Machine Variation Horizontal Distribution screen showing summary information about the horizontal distribution of glass in the glass containers produced by the I.S. machine.
Figure 38:
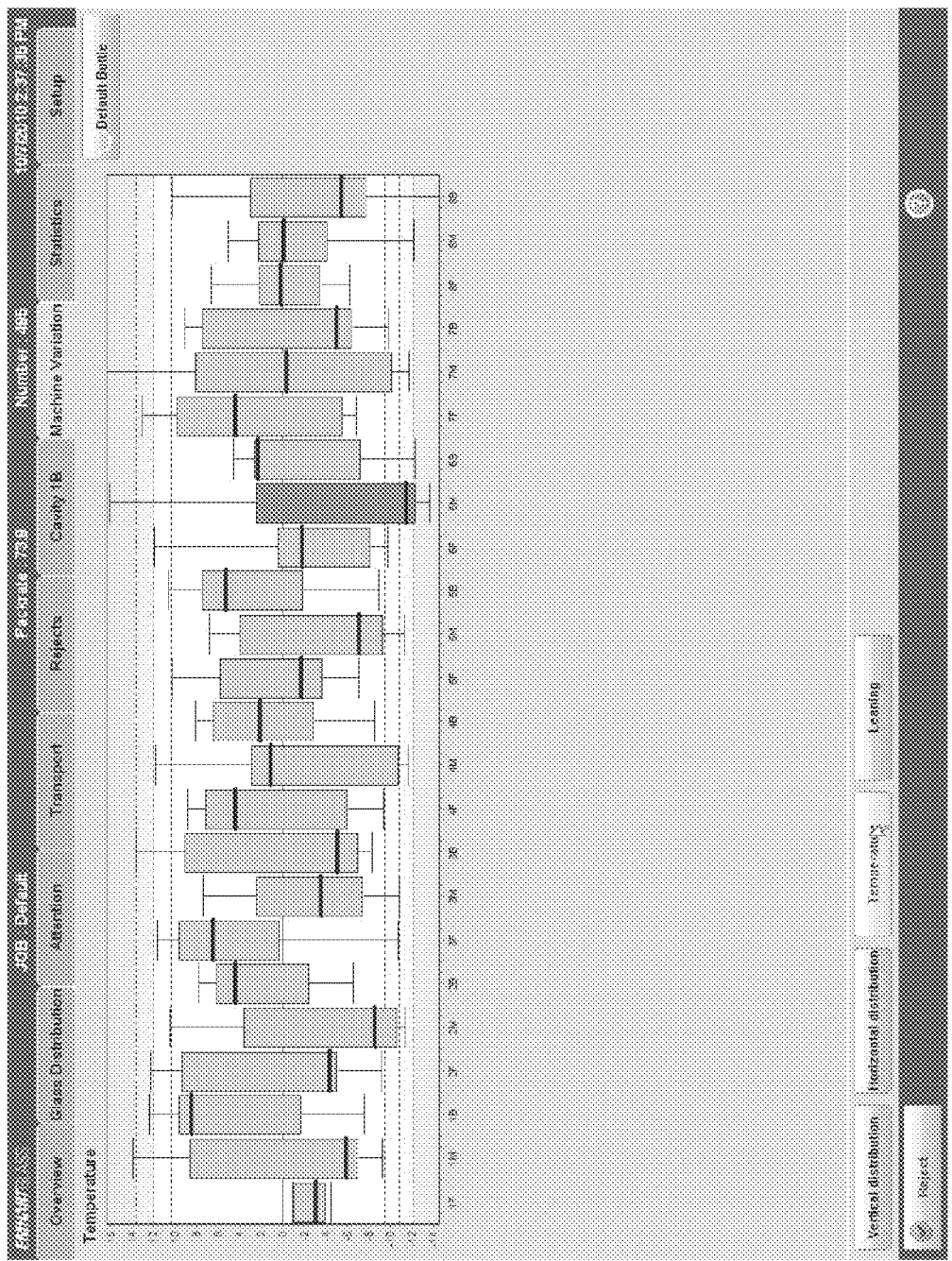
FIG. 38 is a screenshot of the Machine Variation Temperature screen showing summary information about the temperature of glass in the glass containers produced by the I.S. machine.
Figure 39:
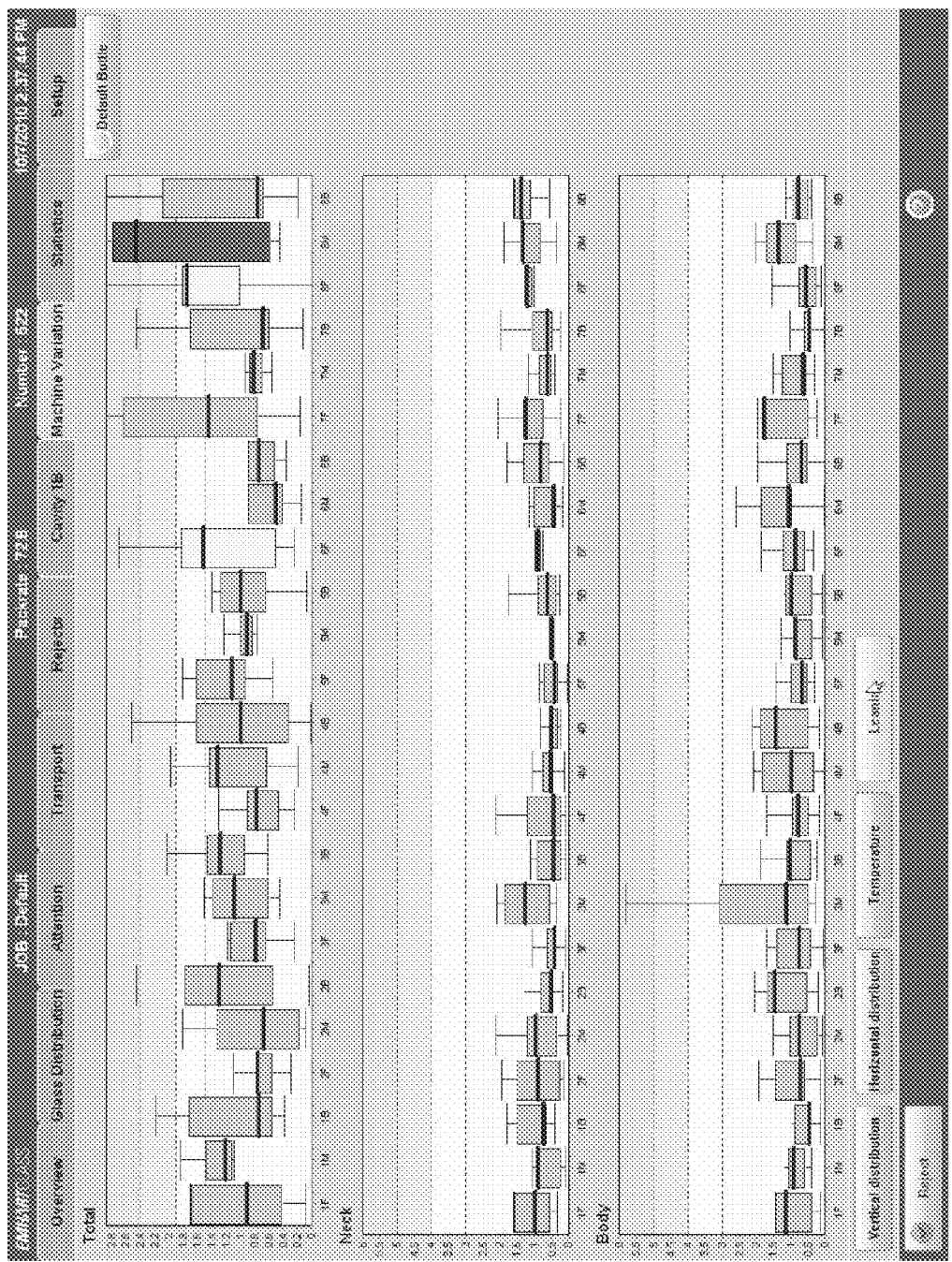
FIG. 39 is a screenshot of the Machine Variation Leaning screen showing summary information about the leaning of glass in the glass containers produced by the I.S. machine.

Referring now to FIGS. 34 and 35, a Section Summary screen is shown for a particular section in FIG. 34, and in FIG. 35 a Section Summary Help screen is shown as being superimposed upon the Section Summary screen of FIG. 34. The Section Summary screen shows a variety of information for the section, including Vertical Glass Distribution, Horizontal Glass Distribution, Glass Distribution, Temperature, and Leaning. For Vertical Glass Distribution, Horizontal Glass Distribution, Temperature, and Leaning, the circle (dot) represents the most recent hot glass container from the section and mold, and the boxplots show the variation for the last predetermined period (e.g., thirty minutes) as well as the median value for that predetermined period.

Referring next to FIGS. 36, 37, 38, and 39, Machine Variation screens are shown for Vertical Glass Distribution, Horizontal Glass Distribution, Temperature, and Leaning, respectively, for each of eight regions in the hot glass containers from the top to the bottom thereof. The boxplots again show the variation for the last predetermined period (e.g., thirty minutes) as well as the median value for that predetermined period.

Figure 40:
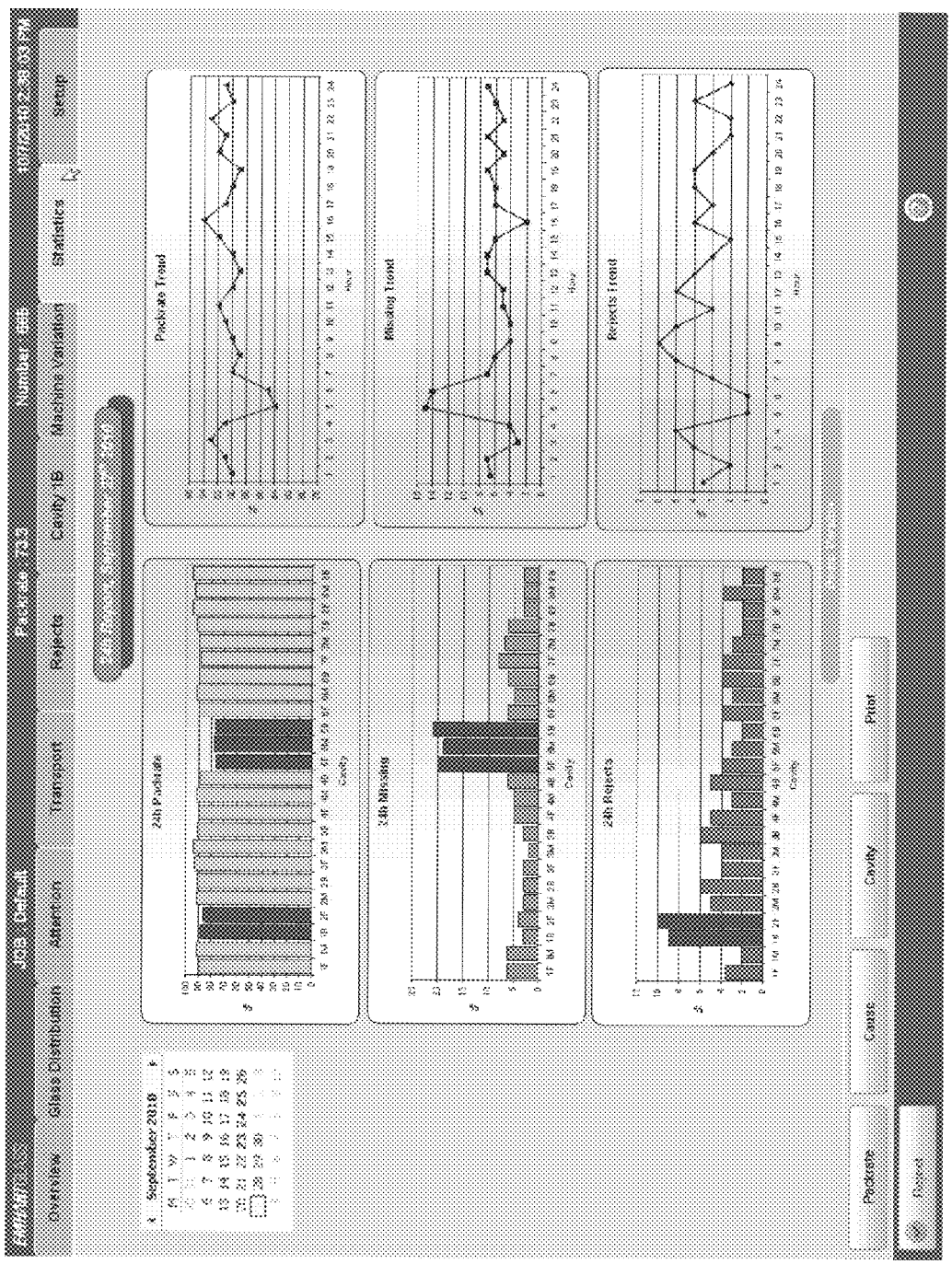
FIG. 40 is a screenshot of the Statistics screen showing summary graphical information regarding the operation of the I.S. machine.

Finally, FIG. 40 shows a Statistics screen displaying summary information for the I.S. machine in graphical form for a predetermined period. This screen is particularly useful for daily production meetings, and can have its period of data collection set appropriately for such a meeting.

Although the foregoing description of the hot glass container quality analytical system of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

What is claimed is:

1. A method for monitoring and analyzing characteristics of hot glass containers formed by an I.S. machine, the method comprising:

monitoring, with at least one imaging device, radiation emitted by hot glass containers after they are formed and before they are cooled as they are conveyed from the I.S. machine on a conveyor;

extracting an individual image of each of the hot glass containers from the monitored radiation emitted by the hot glass containers;

analyzing each individual extracted image to identify the presence or lack of deviations in the glass forming process in each of a plurality of characteristics of the hot glass containers by comparing each characteristic of the hot glass container with the median one of the values for that characteristic in a plurality of hot glass containers immediately preceding the hot glass container being evaluated;

displaying one or more of the individual extracted images of the hot glass containers in real time on display;

simultaneously displaying on the display diagnostic information representative of one or more of the characteristics of the or each hot glass container corresponding to the or each extracted image shown on the display and indicative of the presence or lack of a deviation in the at least one characteristic;

wherein the median value for each of the plurality of characteristics is the median value of the values of that characteristic for a predetermined number of preceding containers, the method including updating the median value for each of the plurality of characteristics by removing the value of the characteristic for the oldest analyzed container of the predetermined number of preceding containers, including the value of the characteristic for the newest analyzed container in the predetermined number of preceding containers, and updating the median value based on the updated values of the characteristic for the updated predetermined number of preceding containers storing diagnostic information representative of one or more of the characteristics of each of the hot glass containers for a predetermined period in a first in, first out database;

determining the median of the diagnostic information representative of one or more of the characteristics of each of the hot glass containers for a predetermined period stored in the first in, first out database;

comparing the diagnostic information representative of one or more of the characteristics of each of the hot glass containers with the median; and wherein a boxplot of the diagnostic information representative of one or more of the characteristics of each of the hot glass containers for a predetermined period stored in the first in, first out database and its median are displayed together with the diagnostic information representative of the one or more of the characteristics of each of the hot glass containers on the display.

2. A method as claimed in claim 1, wherein the at least one imaging device comprises:
a Short Wave Infrared (SWIR) camera.

3. A method as claimed in claim 1, wherein the at least one imaging device comprises:
first and second imaging devices positioned directly after the I.S. machine on opposing sides of and at different angles with respect to the conveyor and to the hot glass container being monitored.

4. A method as defined in claim 1, wherein the analyzing step comprises:
determining the dimensional outline of each hot glass container from the individual extracted image of the hot glass container; and
analyzing the dimensional outline of the hot glass container to determine whether the hot glass container is "stuck ware", "down ware", or "missing".

5. A method as defined in claim 1, wherein the analyzing step comprises:
determining the dimensional outline of each hot glass container from the individual extracted image of the hot glass container; and
analyzing the dimensional outline of the hot glass container to determine any lean in the hot glass container;
wherein the lean of the glass container is displayed on the screen as diagnostic information.

6. A method as defined in claim 1, wherein the analyzing step comprises:
determining the vertical distribution of glass in each hot glass container from the individual extracted image of the hot glass container;
wherein the vertical distribution of glass in the glass container is displayed on the screen as diagnostic information.

7. A method as defined in claim 1, wherein the analyzing step comprises:
determining the horizontal distribution of glass in each hot glass container from the individual extracted image of the hot glass container;
wherein the vertical distribution of glass in the glass container is displayed on the screen as diagnostic information.

8. A method as defined in claim 1, wherein the analyzing step comprises:
determining the vertical distribution of glass in each hot glass container from the individual extracted image of the hot glass container;
determining the horizontal distribution of glass in each hot glass container from the individual extracted image of the hot glass container;
wherein the vertical distribution and the horizontal distribution of glass in the glass container are both displayed on the screen as diagnostic information as a single display element.

9. A method as defined in claim 1, wherein the analyzing step comprises:
setting at least one programmable horizontal region on the images of the hot glass containers at a selected height on the images of the hot glass containers, the programmable horizontal region having a programmable height of at least one horizontal scan line;
determining a diameter of each hot glass container at each programmable horizontal region from the individual extracted image of the hot glass container; and
providing at least one of the determined diameter or information relating to the presence or lack of a deviation in the determined diameter for the hot glass container to the display.

10. A method as defined in claim 9, wherein the at least one imaging device comprises:
first and second imaging devices positioned directly after the I.S. machine on opposing sides of and at different angles with respect to the conveyor on which the hot glass containers are conveyed from the I.S. machine;
determining a diameter of each hot glass container at each programmable horizontal region from the individual extracted images of the hot glass container from each of the first and second imaging devices; and
if the diameters determined from the first and second imaging devices vary more than a predetermined amount for a hot glass container, providing an alarm or warning or rejecting the hot glass container.

11. A method as defined in claim 1, wherein the analyzing step comprises:
assigning a color to each of a plurality of ranges of radiation emitted by hot glass containers;
generating a color image from each extracted image of the hot glass containers by assigning the color associated with the range of radiation for each pixel of the individual extracted images of the hot glass containers;
wherein the displaying step comprises displaying the color image generated from the individual extracted images of the hot glass containers.

12. A method as defined in claim 1, wherein the I.S. machine has a determined number of sections and a determined number of molds in each section, wherein the analyzing step comprises:
determining temperature diagnostic information representative of the temperatures of each of the hot glass containers by calculating the sum of the digital values of all of the pixels on all of a plurality of horizontal scan lines on the image of each glass container;
determining, for each mold, the median value of the temperature diagnostic information representative of the temperatures of each of the hot glass containers for a predetermined period stored in a first in, first out database;

plotting the median values by mold from the coolest mold to the hottest mold, and plotting a best fit line from the median values; and determining, for each mold, the difference between the temperature diagnostic information representative of the temperatures of each of the hot glass containers and the best fit line at the location of the same mold.

13. A method as defined in claim 1, wherein the I.S. machine has a determined number of sections and a determined number of molds in each section, wherein the displaying step comprises:

simultaneously displaying an individual extracted image of a hot glass container formed in each of the molds in each of the sections on the screen, and updating the displayed individual extracted image of a hot glass container formed in each of the molds in each of the sections in real time.

14. A method as defined in claim 1, wherein the I.S. machine has a determined number of sections and a determined number of molds in each section, wherein the displaying step comprises:

simultaneously displaying the three individual extracted images of the hot glass containers from the three molds having the greatest deviations in the at least one characteristic.

15. A method as defined in claim 1, wherein the analyzing step comprises:

determining the location of each of the hot glass containers on the conveyor;

wherein the position of each of the hot glass containers is displayed on the screen.

16. A method as defined in claim 1, wherein if the comparison of the diagnostic information representative of one or more of the characteristics of a hot glass container with the median exceeds a predetermined percentage, an alarm or warning is provided or the hot glass container is rejected.

17. A method as defined in claim 1, additionally comprising:

using the diagnostic information to automatically control the forming process in the I.S. machine.

18. A method as defined in claim 1, wherein the display comprises:

a touchscreen user interface.

19. The method of claim 1, further comprising updating the median value for each characteristic based on the value for each characteristic in each subsequent container.

20. The method of claim 1, wherein the plurality of characteristics include at least one of diameter, vertical distribution of glass, horizontal distribution of glass, and lean.

21. The method of claim 1, further comprising normalizing image information from each individual extracted image.

22. The method of claim 1, further comprising determining a value for one of the characteristics for each of a plurality of consecutive containers and based on the value for the one of the characteristics for each of the plurality of consecutive containers determining the median of the values.

23. A method for monitoring and analyzing characteristics of hot glass containers formed by an I.S. machine, the method comprising:

monitoring, with at least one imaging device, radiation emitted by hot glass containers after they are formed and before they are cooled as they are conveyed from the I.S. machine on a conveyor;

extracting an individual image of each of the hot glass containers from the monitored radiation emitted by the hot glass containers;

analyzing each individual extracted image to identify the presence or lack of deviations in the glass forming process in each of a plurality of characteristics of the hot glass containers by comparing each characteristic of the hot glass container with the median one of the values for that characteristic in a plurality of hot glass containers immediately preceding the hot glass container being evaluated;

displaying one or more of the individual extracted images of the hot glass containers in real time on display;

simultaneously displaying on the display diagnostic information representative of one or more of the characteristics of the or each hot glass container corresponding to the or each extracted image shown on the display and indicative of the presence or lack of a deviation in the at least one characteristic;

wherein the median value for each of the plurality of characteristics is the median value of the values of that characteristic for a predetermined number of preceding containers, the method including updating the median value for each of the plurality of characteristics by removing the value of the characteristic for the oldest analyzed container of the predetermined number of preceding containers, including the value of the characteristic for the newest analyzed container in the predetermined number of preceding containers, and updating the median value based on the updated values of the characteristic for the updated predetermined number of preceding containers;

wherein the diagnostic information simultaneously displayed on the display in a section summary mode comprises: and at least three of Vertical Glass Distribution, Horizontal Glass Distribution, Glass Distribution, Temperature, and Leaning.

24. A system for monitoring and analyzing characteristics of hot glass containers formed by an I.S. machine, the system comprising:

at least one imaging device which monitors the radiation emitted by hot glass containers immediately after the are formed and before they are cooled as the are conveyed from the I.S. machine on a conveyor;

an image extraction module that extracts an individual image of each of the hot glass containers from the monitored radiation emitted by the hot glass containers;

an image processing module that analyzes each individual extracted image to identify the presence or lack of deviations in the glass forming process in each of a plurality of characteristics of the hot glass containers by comparing each characteristic of the hot glass container with the median one of the values for that characteristic in a plurality of hot glass containers immediately preceding the hot class container being evaluated; and a display on which at least one of the individual extracted images of the hot glass containers are displayed in real time;

wherein diagnostic information representative of at least one of the characteristics of the or each hot glass container corresponding to the or each individual extracted image shown on the display and indicative of the presence or lack of a deviation in the at least one characteristic from the median values for those characteristics is simultaneously displayed on the display;

wherein the image processing module comprises: a first in, first out database that stores diagnostic information representative of one or more of the characteristics of each of the hot glass containers for a predetermined period;

wherein the image processing module determines the median of the diagnostic information representative of one or more of the characteristics of each of the hot glass containers for a predetermined period stored in the first in, first out database, and compares the diagnostic information representative of one or more of the characteristics of each of the hot glass containers with the median; and wherein a boxplot of the diagnostic information representative of one or more of the characteristics of each of the hot glass containers for a predetermined period stored in the first in, first out database and its median are displayed together with the diagnostic information representative of the one or more of the characteristics of each of the hot glass containers on the display.

25. A system as defined in claim 24, wherein the at least one imaging device comprises:
a Short Wave Infrared (SWIR) camera.

26. A system as defined in claim 24, wherein the at least one imaging device comprises:
first and second imaging devices positioned directly after the I.S. machine on opposing sides of and at different angles with respect to the conveyor and to a hot glass container when positioned to be monitored.

27. A system as defined in claim 24, wherein the analyzer comprises:
an outline determination module that determines the dimensional outline of each hot glass container from the individual extracted image of the hot glass container; and
a module that analyzes the dimensional outline of the hot glass container to determine whether the hot glass container is "stuck ware", "down ware", or "missing".

28. A system as defined in claim 24, wherein the image processing module comprises:
an outline determination module that determines the dimensional outline of each hot glass container from the individual extracted image of the hot glass container; and
a lean determination module that analyzes the dimensional outline of the hot glass container to determine any lean in the hot glass container;
wherein the lean of the glass container is displayed on the screen as diagnostic information.

29. A system as defined in claim 24, wherein the image processing module comprises:
a vertical distribution determination module that determines the vertical distribution of glass in each hot glass container from the individual extracted image of the hot glass container;
wherein the vertical distribution of glass in the glass container is displayed on the screen as diagnostic information.

30. A system as defined in claim 24, wherein the image processing module comprises:
a horizontal distribution determination module that determines the horizontal distribution of glass in each hot glass container from the individual extracted image of the hot glass container;
wherein the horizontal distribution of glass in the glass container is displayed on the screen as diagnostic information.

31. A system as defined in claim 24, wherein the image processing module comprises:
a vertical distribution determination module that determines the vertical distribution of glass in each hot glass container from the individual extracted image of the hot glass container;
a horizontal distribution determination module that determines the horizontal distribution of glass in each hot glass container from the individual extracted image of the hot glass container;
wherein the vertical distribution and the horizontal distribution of glass in the glass container are both displayed on the screen as diagnostic information as a single display element.

32. A system as defined in claim 24, wherein the image processing module comprises:
a database containing at least one programmable horizontal region on the images of the hot glass containers at a selected height on the images of the hot glass containers, the programmable horizontal region having a programmable height of at least one horizontal scan line; and
a diameter determination module that determines a diameter of each hot glass container at each programmable horizontal region from the individual extracted image of the hot glass container;
wherein diagnostic information representative of at least one of the determined diameter or information relating to the presence or lack of a deviation in the determined diameter for the hot glass container is provided to the display.

33. A system as defined in claim 32, wherein the at least one imaging device comprises:
first and second imaging devices positioned directly after the I.S. machine on opposing sides of and at different angles with respect to the conveyor on which the hot glass containers are conveyed from the I.S. machine;
wherein the diameter determination module that determines a diameter of each hot glass container at each programmable horizontal region from the individual extracted images of the hot glass container from each of the first and second imaging devices; and
wherein if the diameters determined from the first and second imaging devices vary more than a predetermined amount for a hot glass container, an alarm or warning is provided or the hot glass container is rejected.

34. A system as defined in claim 24, wherein the image processing module assigns a color to each of a plurality of ranges of radiation emitted by hot glass containers, and wherein the image processing module generates a color image from each extracted image of the hot glass containers by assigning the color associated with the range of radiation for each pixel of the individual extracted images of the hot glass containers; and
wherein the color image generated from the individual extracted images of the hot glass containers are displayed on the display.

35. A system as defined in claim 24, wherein the I.S. machine has a determined number of sections and a determined number of molds in each section, wherein the image processing module determines temperature diagnostic information representation of the temperatures of each of the hot glass containers by calculating the sum of the digital values of all of the pixels on all of the horizontal scan lines on the image of each glass container;

wherein the image processing module determines, for each mold, the median value of the temperature diagnostic information representative of the temperatures of each of the hot glass containers for a predetermined period stored in a first in, first out database;

wherein the image processing module plots the median values by mold from the coolest mold to the hottest mold, and plots a best fit line from the median values; and wherein the image processing module determines, for each mold, the difference between the temperature diagnostic information representative of the temperatures of each of the hot glass containers and the best fit line at the location of the same mold.

36. A system as defined in claim 24, wherein the I.S. machine has a determined number of sections and a determined number of molds in each section, wherein the display simultaneously displays an individual extracted image of a hot glass container formed in each of the molds in each of the sections on the screen, and the displayed individual extracted image of a hot glass container formed in each of the molds in each of the sections is updated in real time.

37. A system as defined in claim 24, wherein the I.S. machine has a determined number of sections and a determined number of molds in each section, wherein the display simultaneously displays the three individual extracted images of the hot glass containers from the three molds having the greatest deviations in the at least one characteristic.

38. A system as defined in claim 24, wherein the image processing module comprises:

a product location module for determining the location of each of the hot glass containers on the conveyor;

wherein information representative of the position of each of the hot glass containers is provided to the display.

39. A system as defined in claim 24, wherein if the comparison of the diagnostic information representative of one or more of the characteristics of a hot glass container with the median exceeds a predetermined percentage, an alarm or warning is provided or the hot glass container is rejected.

40. A system as defined in claim 24, wherein the display has a section summary mode in which at least three of Vertical Glass Distribution, Horizontal Glass Distribution, Glass Distribution, Temperature, and Leaning are simultaneously displayed on the display.

41. A system as defined in claim 24, additionally comprising:

an I.S. machine control unit that uses the diagnostic information to automatically control the forming process in the I.S. machine.

42. A system as defined in claim 24, wherein the display comprises:

a touchscreen user interface.

\* \* \* \* \*

UNITED STATES PATENT AND TRADEMARK OFFICE
CERTIFICATE OF CORRECTION

PATENT NO. : 9,671,357 B2
APPLICATION NO. : 12/963405
DATED : June 6, 2017
INVENTOR(S) : Mark Edwin Holtkamp et al.

It is certified that error appears in the above-identified patent and that said Letters Patent is hereby corrected as shown below:

On the Title Page

Item (73) Assignee: "Emhardt Glass S.A." should correctly read --Emhart Glass S.A.--

In the Claims

Column 24 Claim 1, Line 56, "real time on display" should read --real time on a display--

Column 28 Claim 23, Line 17, "real time on display" should read --real time on a display--

Column 28 Claim 24, Line 47, "immediately after the" should read --immediately after they--

Column 28 Claim 24, Line 48, "are cooled as the" should read --are cooled as they--

Column 28 Claim 24, Line 60, "hot class" should read --hot glass--

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*